(12) United States Patent
Duindam

(10) Patent No.: US 10,682,070 B2
(45) Date of Patent: Jun. 16, 2020

(54) ELECTROMAGNETIC SENSOR WITH PROBE AND GUIDE SENSING ELEMENTS

(71) Applicant: Intuitive Surgical Operations, Inc., Sunnyvale, CA (US)

(72) Inventor: Vincent Duindam, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 507 days.

(21) Appl. No.: 14/802,199

(22) Filed: Jul. 17, 2015

(65) Prior Publication Data

US 2016/0007880 A1 Jan. 14, 2016

Related U.S. Application Data

(60) Division of application No. 13/889,984, filed on May 8, 2013, now abandoned, which is a
(Continued)

(51) Int. Cl.
*A61B 5/06* (2006.01)
*A61M 25/09* (2006.01)
(Continued)

(52) U.S. Cl.
CPC .............. *A61B 5/062* (2013.01); *A61B 5/065* (2013.01); *A61B 34/20* (2016.02); *A61M 25/09* (2013.01);
(Continued)

(58) Field of Classification Search
None
See application file for complete search history.

(56) References Cited

U.S. PATENT DOCUMENTS 3,096,962 A 7/1963 Meijs
3,546,961 A 12/1970 Marton
(Continued)

FOREIGN PATENT DOCUMENTS

CN 101088451 A 12/2007
CN 101247847 A 8/2008
(Continued)

OTHER PUBLICATIONS

Abbott, Daniel J. et al., "Design of an Endoluminal NOTES Robotic System," Conference on Intelligent Robots and Systems, 2007, pp. 410-416.
(Continued)

*Primary Examiner* — Matthew Kremer
(74) *Attorney, Agent, or Firm* — Haynes and Boone, LLP

(57) ABSTRACT

A medical system comprises a probe comprising a terminal distal end. The system further comprises a first coil in the probe and comprises a guide instrument including a terminal distal end and defining a lumen sized to guide the probe. The probe can be inserted through the lumen to reach a worksite. At the worksite, the terminal distal end of the probe is configured to reach at least the terminal distal end of the guide instrument. The system further comprises a sensor embedded in a wall of the guide instrument and comprises processing hardware configured to receive a first induced signal from the first coil and to receive from the sensor an indication of a pointing direction of the guide instrument. The processing hardware is configured to use the first induced signal and the indication of the pointing direction to determine a roll angle of the probe.

20 Claims, 4 Drawing Sheets

Related U.S. Application Data continuation-in-part of application No. 13/274,237, filed on Oct. 14, 2011, now Pat. No. 9,387,048.

(60) Provisional application No. 61/646,619, filed on May 14, 2012.

(51) Int. Cl.
*A61B 34/20* (2016.01)
*A61M 25/01* (2006.01)
*A61B 5/00* (2006.01)
*A61B 34/30* (2016.01)

(52) U.S. Cl.
CPC ..... *A61B 5/6852* (2013.01); *A61B 2034/2051* (2016.02); *A61B 2034/302* (2016.02); *A61M 2025/0166* (2013.01)

(56) References Cited

U.S. PATENT DOCUMENTS

| | | |
|---|---|---|
| 4,437,114 A | 3/1984 | Larussa |
| 4,792,715 A | 12/1988 | Barsky et al. |
| 4,809,191 A | 2/1989 | Domeier et al. |
| 4,905,082 A | 2/1990 | Nishigaki et al. |
| 4,949,927 A | 8/1990 | Madocks et al. |
| 5,114,403 A | 5/1992 | Clarke et al. |
| 5,174,276 A | 12/1992 | Crockard |
| 5,201,757 A | 4/1993 | Heyn et al. |
| 5,251,611 A | 10/1993 | Zehel et al. |
| 5,285,796 A | 2/1994 | Hughes |
| 5,297,536 A | 3/1994 | Wilk |
| 5,307,437 A | 4/1994 | Facq et al. |
| 5,351,693 A | 10/1994 | Taimisto et al. |
| 5,417,210 A | 5/1995 | Funda et al. |
| 5,429,604 A | 7/1995 | Hammersmark et al. |
| 5,487,757 A | 1/1996 | Truckai et al. |
| 5,588,949 A | 12/1996 | Taylor et al. |
| 5,613,946 A | 3/1997 | Mckeever |
| 5,617,515 A | 4/1997 | Maclaren et al. |
| 5,624,380 A | 4/1997 | Takayama et al. |
| 5,643,175 A | 7/1997 | Adair |
| 5,729,129 A | 3/1998 | Acker |
| 5,752,112 A | 5/1998 | Paddock et al. |
| 5,755,713 A | 5/1998 | Bilof et al. |
| 5,759,151 A | 6/1998 | Sturges |
| 5,792,135 A | 8/1998 | Madhani et al. |
| 5,797,900 A | 8/1998 | Madhani et al. |
| 5,817,084 A | 10/1998 | Jensen |
| 5,855,569 A | 1/1999 | Komi |
| 5,868,760 A | 2/1999 | Mcguckin, Jr. |
| 5,876,325 A | 3/1999 | Mizuno et al. |
| 5,892,860 A | 4/1999 | Maron et al. |
| 5,899,425 A | 5/1999 | Corey, Jr. et al. |
| 5,976,071 A | 11/1999 | Sekiya |
| 5,982,791 A | 11/1999 | Sorin et al. |
| 6,013,024 A | 1/2000 | Mitsuda et al. |
| 6,030,130 A | 2/2000 | Paddock et al. |
| 6,066,090 A | 5/2000 | Yoon |
| 6,120,433 A | 9/2000 | Mizuno et al. |
| 6,132,368 A | 10/2000 | Cooper |
| 6,161,032 A | 12/2000 | Acker |
| 6,171,277 B1 | 1/2001 | Ponzi |
| 6,188,355 B1 | 2/2001 | Gilboa |
| 6,191,414 B1 | 2/2001 | Ogle et al. |
| 6,200,274 B1 | 3/2001 | Mcneirney |
| 6,203,493 B1 | 3/2001 | Ben-Haim |
| 6,253,770 B1 * | 7/2001 | Acker ............... A61B 1/31 128/899 |
| 6,275,628 B1 | 8/2001 | Jones et al. |
| 6,331,181 B1 | 12/2001 | Tierney et al. |
| 6,332,089 B1 | 12/2001 | Acker et al. |
| 6,335,617 B1 | 1/2002 | Osadchy et al. |
| 6,347,892 B1 | 2/2002 | Paddock et al. |
| 6,352,503 B1 | 3/2002 | Matsui et al. |
| 6,366,722 B1 | 4/2002 | Murphy et al. |
| 6,366,799 B1 | 4/2002 | Acker et al. |
| 6,371,952 B1 | 4/2002 | Madhani et al. |
| 6,380,732 B1 | 4/2002 | Gilboa |
| 6,389,187 B1 | 5/2002 | Greenaway et al. |
| 6,396,574 B1 | 5/2002 | Lee et al. |
| 6,432,041 B1 | 8/2002 | Taniguchi et al. |
| 6,441,577 B2 | 8/2002 | Blumenkranz et al. |
| 6,451,027 B1 | 9/2002 | Cooper et al. |
| 6,453,190 B1 | 9/2002 | Acker et al. |
| 6,470,205 B2 | 10/2002 | Bosselmann et al. |
| 6,471,710 B1 | 10/2002 | Bucholtz |
| 6,478,028 B1 | 11/2002 | Paolitto et al. |
| 6,484,118 B1 | 11/2002 | Govari |
| 6,487,352 B1 | 11/2002 | Sobiski et al. |
| 6,490,467 B1 | 12/2002 | Bucholz et al. |
| 6,554,793 B1 | 4/2003 | Pauker et al. |
| 6,571,639 B1 | 6/2003 | May et al. |
| 6,572,629 B2 | 6/2003 | Kalloo et al. |
| 6,574,355 B2 | 6/2003 | Green |
| 6,575,644 B2 | 6/2003 | Paddock et al. |
| 6,578,967 B1 | 6/2003 | Paddock et al. |
| 6,618,612 B1 | 9/2003 | Acker et al. |
| 6,645,196 B1 | 11/2003 | Nixon et al. |
| 6,648,816 B2 | 11/2003 | Irion et al. |
| 6,671,055 B1 | 12/2003 | Wavering et al. |
| 6,671,581 B2 | 12/2003 | Niemeyer et al. |
| 6,695,871 B1 | 2/2004 | Maki et al. |
| 6,720,988 B1 | 4/2004 | Gere et al. |
| 6,743,239 B1 | 6/2004 | Kuehn et al. |
| 6,758,843 B2 | 7/2004 | Jensen |
| 6,783,491 B2 | 8/2004 | Saadat et al. |
| 6,790,173 B2 | 9/2004 | Saadat et al. |
| 6,817,974 B2 | 11/2004 | Cooper et al. |
| 6,833,814 B2 | 12/2004 | Gilboa et al. |
| 6,837,847 B2 | 1/2005 | Ewers et al. |
| 6,866,671 B2 | 3/2005 | Tierney et al. |
| 6,899,672 B2 | 5/2005 | Chin et al. |
| 6,902,560 B1 | 6/2005 | Morley et al. |
| 6,936,042 B2 | 8/2005 | Wallace et al. |
| 6,942,613 B2 | 9/2005 | Ewers et al. |
| 6,960,162 B2 | 11/2005 | Saadat et al. |
| 6,960,163 B2 | 11/2005 | Ewers et al. |
| 6,984,203 B2 | 1/2006 | Tartaglia et al. |
| 6,991,602 B2 | 1/2006 | Nakazawa et al. |
| 6,994,703 B2 | 2/2006 | Wang et al. |
| 6,997,870 B2 | 2/2006 | Couvillon, Jr. |
| 7,007,699 B2 | 3/2006 | Martinelli et al. |
| 7,041,052 B2 | 5/2006 | Saadat et al. |
| 7,042,573 B2 | 5/2006 | Froggatt |
| 7,090,637 B2 | 8/2006 | Danitz et al. |
| 7,090,683 B2 | 8/2006 | Brock et al. |
| 7,128,708 B2 | 10/2006 | Saadat et al. |
| 7,139,601 B2 | 11/2006 | Bucholz et al. |
| 7,197,354 B2 | 3/2007 | Sobe |
| 7,233,820 B2 | 6/2007 | Gilboa |
| 7,252,660 B2 | 8/2007 | Kunz |
| 7,277,120 B2 | 10/2007 | Gere et al. |
| 7,320,700 B2 | 1/2008 | Cooper et al. |
| 7,371,028 B2 | 5/2008 | Gordon et al. |
| 7,398,116 B2 | 7/2008 | Edwards |
| 7,500,947 B2 | 3/2009 | Kucklick et al. |
| 7,594,912 B2 | 9/2009 | Cooper et al. |
| 7,715,105 B2 | 5/2010 | Forkey et al. |
| 7,720,322 B2 | 5/2010 | Prisco |
| 7,725,214 B2 | 5/2010 | Diolaiti |
| 7,853,307 B2 | 12/2010 | Edwards |
| 7,920,909 B2 | 4/2011 | Lyon et al. |
| 7,922,650 B2 | 4/2011 | Mcweeney et al. |
| 7,930,065 B2 | 4/2011 | Larkin et al. |
| 7,947,000 B2 | 5/2011 | Vargas et al. |
| 7,962,193 B2 | 6/2011 | Edwards et al. |
| 8,016,749 B2 | 9/2011 | Clerc et al. |
| 8,784,303 B2 | 7/2014 | Laby et al. |
| 8,784,435 B2 | 7/2014 | Cooper et al. |
| 8,858,424 B2 | 10/2014 | Hasegawa et al. |
| 9,060,678 B2 | 6/2015 | Larkin et al. |
| 9,125,639 B2 | 9/2015 | Mathis et al. |
| 9,387,048 B2 | 7/2016 | Donhowe et al. |

(56) References Cited

U.S. PATENT DOCUMENTS

| | | |
|---|---|---|
| 9,452,276 B2 | 9/2016 | Duindam et al. |
| 10,080,576 B2 | 9/2018 | Romo et al. |
| 10,238,837 B2 | 3/2019 | Duindam et al. |
| 2001/0049509 A1 | 12/2001 | Sekine et al. |
| 2002/0077550 A1 | 6/2002 | Rabiner et al. |
| 2002/0087169 A1 | 7/2002 | Brock et al. |
| 2002/0120252 A1 | 8/2002 | Brock et al. |
| 2002/0143319 A1 | 10/2002 | Brock |
| 2002/0151967 A1 | 10/2002 | Mikus et al. |
| 2002/0156345 A1 | 10/2002 | Eppler et al. |
| 2002/0173786 A1 | 11/2002 | Kortenbach et al. |
| 2003/0050649 A1 | 3/2003 | Brock et al. |
| 2003/0236455 A1 | 12/2003 | Swanson et al. |
| 2003/0236505 A1 | 12/2003 | Bonadio et al. |
| 2004/0024311 A1 | 2/2004 | Quaid et al. |
| 2004/0054355 A1 | 3/2004 | Gerbi et al. |
| 2004/0083808 A1 | 5/2004 | Rambow et al. |
| 2004/0116803 A1 | 6/2004 | Jascob et al. |
| 2004/0138525 A1 | 7/2004 | Saadat et al. |
| 2004/0138529 A1 | 7/2004 | Wiltshire et al. |
| 2004/0147837 A1 | 7/2004 | Macaulay et al. |
| 2004/0153191 A1 | 8/2004 | Grimm et al. |
| 2004/0202400 A1 | 10/2004 | Kochergin et al. |
| 2004/0249367 A1 | 12/2004 | Saadat et al. |
| 2005/0004431 A1 | 1/2005 | Kogasaka et al. |
| 2005/0043718 A1 | 2/2005 | Madhani et al. |
| 2005/0049486 A1 | 3/2005 | Urquhart et al. |
| 2005/0059960 A1 | 3/2005 | Simaan et al. |
| 2005/0065397 A1 | 3/2005 | Saadat et al. |
| 2005/0065398 A1 | 3/2005 | Adams |
| 2005/0096502 A1 | 5/2005 | Khalili |
| 2005/0102062 A1 | 5/2005 | Green |
| 2005/0131343 A1 | 6/2005 | Abrams et al. |
| 2005/0192532 A1 | 9/2005 | Kucklick et al. |
| 2005/0197536 A1 | 9/2005 | Banik et al. |
| 2005/0197557 A1 | 9/2005 | Strommer et al. |
| 2005/0215983 A1 | 9/2005 | Brock |
| 2005/0222554 A1 | 10/2005 | Wallace et al. |
| 2005/0251176 A1 | 11/2005 | Swanstrom et al. |
| 2005/0272977 A1* | 12/2005 | Saadat ............... A61B 1/0008 600/114 |
| 2005/0284221 A1 | 12/2005 | Danisch et al. |
| 2006/0013523 A1 | 1/2006 | Childers et al. |
| 2006/0025652 A1 | 2/2006 | Vargas |
| 2006/0149418 A1 | 7/2006 | Anvari |
| 2006/0161136 A1 | 7/2006 | Anderson et al. |
| 2006/0184016 A1 | 8/2006 | Glossop et al. |
| 2007/0016070 A1 | 1/2007 | Grunwald et al. |
| 2007/0021738 A1 | 1/2007 | Hasser et al. |
| 2007/0049908 A1 | 3/2007 | Boese et al. |
| 2007/0055128 A1 | 3/2007 | Glossop |
| 2007/0055291 A1 | 3/2007 | Birkmeyer et al. |
| 2007/0065077 A1 | 3/2007 | Childers et al. |
| 2007/0083217 A1 | 4/2007 | Eversull et al. |
| 2007/0089557 A1 | 4/2007 | Solomon et al. |
| 2007/0106116 A1 | 5/2007 | Sugimoto |
| 2007/0135803 A1* | 6/2007 | Belson ............... A61B 1/00154 606/1 |
| 2007/0137371 A1 | 6/2007 | Devengenzo et al. |
| 2007/0151391 A1 | 7/2007 | Larkin et al. |
| 2007/0156020 A1 | 7/2007 | Foley et al. |
| 2007/0173694 A1 | 7/2007 | Tsuji et al. |
| 2007/0197896 A1 | 8/2007 | Moll et al. |
| 2007/0225554 A1 | 9/2007 | Maseda et al. |
| 2007/0265503 A1 | 11/2007 | Schlesinger et al. |
| 2007/0270642 A1 | 11/2007 | Bayer et al. |
| 2007/0283970 A1 | 12/2007 | Mohr et al. |
| 2007/0287884 A1 | 12/2007 | Schena |
| 2007/0287889 A1 | 12/2007 | Mohr |
| 2007/0287992 A1 | 12/2007 | Diolaiti et al. |
| 2008/0058861 A1 | 3/2008 | Cooper et al. |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065106 A1 | 3/2008 | Larkin |
| 2008/0065107 A1 | 3/2008 | Larkin et al. |
| 2008/0065109 A1 | 3/2008 | Larkin |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0097155 A1 | 4/2008 | Gattani et al. |
| 2008/0103362 A1 | 5/2008 | Couvillon, Jr. |
| 2008/0147089 A1 | 6/2008 | Loh et al. |
| 2008/0151041 A1 | 6/2008 | Shafer et al. |
| 2008/0156971 A1 | 7/2008 | Ogisu et al. |
| 2008/0172049 A1 | 7/2008 | Bredno et al. |
| 2008/0212082 A1 | 9/2008 | Froggatt et al. |
| 2008/0255505 A1 | 10/2008 | Carlson et al. |
| 2008/0287963 A1 | 11/2008 | Rogers et al. |
| 2009/0030307 A1 | 1/2009 | Govari et al. |
| 2009/0085807 A1 | 4/2009 | Anderson |
| 2009/0088756 A1 | 4/2009 | Anderson |
| 2009/0088774 A1 | 4/2009 | Swarup et al. |
| 2009/0096443 A1 | 4/2009 | Anderson |
| 2009/0105799 A1* | 4/2009 | Hekmat ................ A61B 5/201 623/1.11 |
| 2009/0118620 A1* | 5/2009 | Tgavalekos ............ A61B 5/06 600/463 |
| 2009/0123111 A1 | 5/2009 | Udd |
| 2009/0137952 A1 | 5/2009 | Ramamurthy et al. |
| 2009/0231419 A1 | 9/2009 | Bayer |
| 2009/0248040 A1 | 10/2009 | Cooper et al. |
| 2009/0281566 A1 | 11/2009 | Edwards et al. |
| 2009/0314131 A1 | 12/2009 | Bailey |
| 2009/0322001 A1 | 12/2009 | Luke et al. |
| 2009/0326322 A1 | 12/2009 | Diolaiti |
| 2009/0326552 A1 | 12/2009 | Diolaiti |
| 2009/0326553 A1 | 12/2009 | Mustufa et al. |
| 2010/0076303 A1 | 3/2010 | Mckinley |
| 2010/0082041 A1 | 4/2010 | Prisco |
| 2010/0121139 A1 | 5/2010 | Ouyang et al. |
| 2010/0125284 A1* | 5/2010 | Tanner ................. A61B 34/71 606/130 |
| 2010/0170519 A1 | 7/2010 | Romo et al. |
| 2010/0210939 A1* | 8/2010 | Hartmann ............ A61B 5/062 600/424 |
| 2010/0222647 A1 | 9/2010 | Hashimshony et al. |
| 2010/0274087 A1 | 10/2010 | Diolaiti et al. |
| 2010/0292535 A1 | 11/2010 | Paskar |
| 2010/0331820 A1 | 12/2010 | Prisco et al. |
| 2010/0332033 A1 | 12/2010 | Diolaiti et al. |
| 2011/0021903 A1 | 1/2011 | Strommer et al. |
| 2011/0028991 A1 | 2/2011 | Ikeda et al. |
| 2011/0040305 A1 | 2/2011 | Gomez et al. |
| 2011/0040404 A1 | 2/2011 | Diolaiti et al. |
| 2011/0054309 A1 | 3/2011 | Edwards |
| 2011/0082365 A1 | 4/2011 | Mcgrogan et al. |
| 2011/0092808 A1 | 4/2011 | Shachar et al. |
| 2011/0125032 A1 | 5/2011 | Mcintyre et al. |
| 2011/0152879 A1 | 6/2011 | Williams |
| 2011/0172680 A1 | 7/2011 | Younge et al. |
| 2011/0172687 A1 | 7/2011 | Woodruff et al. |
| 2011/0184241 A1 | 7/2011 | Zubiate et al. |
| 2011/0184276 A1 | 7/2011 | Lyon et al. |
| 2011/0196419 A1 | 8/2011 | Cooper |
| 2011/0201883 A1 | 8/2011 | Cooper et al. |
| 2011/0201922 A1 | 8/2011 | Hezemans et al. |
| 2011/0202068 A1 | 8/2011 | Diolaiti et al. |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |

(56) References Cited

U.S. PATENT DOCUMENTS

| | | | |
|---|---|---|---|
| 2011/0224825 | A1 | 9/2011 | Larkin et al. |
| 2011/0237889 | A1 | 9/2011 | Tanaka |
| 2011/0277576 | A1 | 11/2011 | Cooper |
| 2011/0277579 | A1 | 11/2011 | Anderson et al. |
| 2011/0277580 | A1 | 11/2011 | Cooper et al. |
| 2011/0277775 | A1 | 11/2011 | Holop et al. |
| 2011/0277776 | A1 | 11/2011 | Mcgrogan et al. |
| 2011/0282356 | A1 | 11/2011 | Solomon et al. |
| 2011/0282357 | A1 | 11/2011 | Rogers et al. |
| 2011/0282358 | A1 | 11/2011 | Gomez et al. |
| 2011/0282359 | A1 | 11/2011 | Duval |
| 2011/0282491 | A1 | 11/2011 | Prisco et al. |
| 2012/0010628 | A1 | 1/2012 | Cooper et al. |
| 2012/0046522 | A1 | 2/2012 | Naito |
| 2012/0116393 | A1 | 5/2012 | Jimenez et al. |
| 2012/0123441 | A1 | 5/2012 | Au et al. |
| 2012/0150075 | A1* | 6/2012 | Ludwin ............... A61B 5/065 600/587 |
| 2012/0165608 | A1 | 6/2012 | Banik et al. |
| 2012/0182409 | A1* | 7/2012 | Moriyama ........ A61B 1/00006 348/65 |
| 2012/0289815 | A1 | 11/2012 | Keast et al. |
| 2013/0096377 | A1 | 4/2013 | Duindam et al. |
| 2013/0096385 | A1 | 4/2013 | Fenech et al. |
| 2013/0096497 | A1 | 4/2013 | Duindam et al. |
| 2013/0096572 | A1 | 4/2013 | Donhowe et al. |
| 2013/0144124 | A1 | 6/2013 | Prisco et al. |
| 2013/0169272 | A1* | 7/2013 | Eichler ................ A61B 5/062 324/253 |
| 2013/0172906 | A1 | 7/2013 | Olson et al. |
| 2013/0223702 | A1 | 8/2013 | Holsing et al. |
| 2013/0303944 | A1 | 11/2013 | Duindam |
| 2014/0296872 | A1 | 10/2014 | Cooper et al. |
| 2016/0029998 | A1 | 2/2016 | Brister et al. |
| 2016/0302873 | A1 | 10/2016 | Donhowe et al. |

FOREIGN PATENT DOCUMENTS

| | | |
|---|---|---|
| CN | 101918073 A | 12/2010 |
| JP | S57190549 A | 11/1982 |
| JP | H06285009 A | 10/1994 |
| JP | H07504363 A | 5/1995 |
| JP | H1020214 A | 1/1998 |
| JP | 2000093522 A | 4/2000 |
| JP | 2000166936 A | 6/2000 |
| JP | 2001046529 A | 2/2001 |
| JP | 2003275223 A | 9/2003 |
| JP | 2008018007 A | 1/2008 |
| WO | WO-9313916 A1 | 7/1993 |
| WO | WO-9605768 A1 | 2/1996 |
| WO | WO-9729690 A1 | 8/1997 |
| WO | WO-0051486 A1 | 9/2000 |
| WO | WO-0207809 A1 | 1/2002 |
| WO | WO-2004016155 A2 | 2/2004 |
| WO | WO-2005087128 A1 | 9/2005 |
| WO | WO-2006039092 A2 | 4/2006 |
| WO | WO-2007109418 A2 | 9/2007 |
| WO | WO-2007109778 A1 | 9/2007 |
| WO | WO-2007146987 A2 | 12/2007 |
| WO | WO-2008028149 A2 | 3/2008 |
| WO | WO-2009002701 A2 | 12/2008 |
| WO | WO-2011100110 A1 | 8/2011 |

OTHER PUBLICATIONS

Anisfield, Nancy; "Ascension Technology Puts Spotlight on DC Field Magnetic Motion Tracking," HP Chronicle, Aug. 2000, vol. 17, No. 9, 3 Pages.

Ascari, Luca et al., "A New Active Microendoscope for Exploring the Sub-Arachnoid Space in the Spinal Cord," Proc. IEEE International Conference on Robotics and Automation, 2003, pp. 2657-2662, vol. 2, IEEE.

Barnes Industries, Inc., "How a Ball Screw Works," 4 pages, Copyright 2007; Internet: http://www.barnesballscrew.com/ball.htm.

Berthold III, John W., "Historical Review of Microbend Fiber-Optic Sensors," Journal of Lightwave Technology, vol. 13, No. 7, Jul. 1995, pp. 1193-1199.

Blue Road Research, "Overview of Fiber Optic Sensors," 40 pages, first posted Dec. 8, 2004. Internet <www.bluerr.com/papers/Overview_of_FOS2.pdf>.

Cao, Caroline G.L., "Designing Spatial Orientation in Endoscopic Environments," Proceedings of the Human Factors and Ergonomics Society 45th Annual Meeting, 2001, pp. 1259-1263.

Cao, Caroline G.L., "Disorientation in Minimal Access Surgery: A Case Study," Proceedings of the IEA 2000/HFES 2000 Congress, pp. 4-169-4-172.

Childers, Brooks A., et al, "Use of 3000 Bragg grating strain sensors distributed on four eight-meter optical fibers during static load tests of a composite structure," SPIE 8th International Symposium on Smart Structures and Materials, Mar. 4-8, 2001, Newport Beach, California, 10 Pages.

Choi, Dong-Geol et al., "Design of a Spring Backbone Micro Endoscope," Conference on Intelligent Robots and Systems, 2007, pp. 1815-1821.

U.S. Appl. No. 11/762,185, filed Jun. 13, 2007.
U.S. Appl. No. 60/813,028, filed Jun. 13, 2006.
U.S. Appl. No. 60/813,029, filed Jun. 13, 2006.
U.S. Appl. No. 60/813,030, filed Jun. 13, 2006.
U.S. Appl. No. 60/813,075, filed Jun. 13, 2006.
U.S. Appl. No. 60/813,125, filed Jun. 13, 2006.
U.S. Appl. No. 60/813,126, filed Jun. 13, 2006.
U.S. Appl. No. 60/813,129, filed Jun. 13, 2006.
U.S. Appl. No. 60/813,131, filed Jun. 13, 2006.
U.S. Appl. No. 60/813,172, filed Jun. 13, 2006.
U.S. Appl. No. 60/813,173, filed Jun. 13, 2006.
U.S. Appl. No. 60/813,198, filed Jun. 13, 2006.
U.S. Appl. No. 60/813,207, filed Jun. 13, 2006.
U.S. Appl. No. 60/813,328, filed Jun. 13, 2006.
U.S. Appl. No. 61/334,978, filed May 14, 2010.

Cowie, Barbara M., et al., "Distributive Tactile Sensing Using Fibre Bragg Grating Sensors for Biomedical Applications," 1st IEEE / RAS-EMBS International Conference on Biomedical Robotics and Biomechatronics (BioRob 2006), Feb. 2006, pp. 312-317.

Danisch, Lee et al., "Spatially continuous six degree of freedom position and orientation sensor," Sensor Review, 1999, vol. 19, Issue 2, pp. 106-112.

Dario, Paolo et al., "A Miniature Device for Medical Intracavitary Intervention," Micro Electro Mechanical Systems '91 Proc IEEE 'An Investigation of Micro Structures, Sensors, Actuators, Machines and Robots', 1991, pp. 171-175, IEEE.

Duncan, Roger, "Sensing Shape: Fiber-Bragg-grating sensor arrays monitor shape at a high resolution," 2005, pp. 18-21, SPIE.

Extended European Search Report for Application No. EP20070798487, dated Jan. 30, 2015, 8 pages.

Gagarina, T. et al., "Modeling and experimental analysis of a new bellow type actuators for active catheter end-effector," Proc. 10th IEEE International Workshop on Robot and Human Interactive Communication, 2001, pp. 612-617. IEEE.

Gander, M.J. et al., "Bend measurement using Bragg gratings in multicore fibre," Electronics Letter, Jan. 20, 2000, vol. 36, No. 2, 2 Pages.

Hill, Kenneth O., "Fiber Bragg grating technology fundamentals and overview," IEEE Journal of Lightwave Technology, vol. 15, Issue 8, Aug. 1997, pp. 1263-1276.

Ikuta, Koji et al., "Development of remote microsurgery robot and new surgical procedure for deep and narrow space," Proc. IEEE International Conference on Robotics & Automation, 2003, pp. 1103-1108, vol. 1, IEEE.

Ikuta, Koji et at, "Shape memory alloy servo actuator system with electric resistance feedback and application for active endoscope," Proc. IEEE International Conference on Robotics and Automation, 1988, pp. 427-430, vol. 1, IEEE.

International Search Report and Written Opinion for Application No. PCT/US2012/059889, dated Mar. 29, 2013, 14 pages.

(56) References Cited

OTHER PUBLICATIONS

International Search Report for application No. PCT/US07/71085, dated Sep. 17, 2008, 2 pages.
Jin, Long et at, "Two-dimensional bend sensing with a cantilever-mounted FBG [Fiber Bragg Grating]," Meas. Sci. Technol., 2006, pp. 168-172, vol. 17, Institute of Physics Publishing.
Kreger, Stephen et al., "Optical Frequency Domain Reflectometry for High Density Multiplexing of Multi-Axis Fiber Bragg Gratings," 16th International Conference on Optical Fiber Sensors (OFS-16), Oct. 2003, Nara, Japan, pp. 526-529.
Lertpiriyasuwat, Vatchara et al., "Extended Kalman Filtering Applied to a Two-Axis Robotic Arm with Flexible Links," International Journal of Robotics Research, 2000, vol. 19., No. 3, pp. 254-270.
Martinez, A. et al., "Vector Bending Sensors Based on Fibre Bragg Gratings Inscribed by Infrared Femtosecond Laser," Electronics Letters, 2005, pp. 472-474, vol. 41—Issue 8.
Measurand, "ShapeTape Overview," Measurand ShapeTape Advantage, pp. 1-3, first posted Nov. 3, 2004. Internet <www.measurand.com/products/ShapeTape_overview.html>.
Meltz, Gerald, "Overview of Fiber Grating-Based Sensors," Proceedings of SPIE Distributed Multiplexed Fiber Optic Sensors VI, Nov. 27, 1996, Eds. Kersey et al.,vol. 2838, pp. 2-22.
Office Action dated Jun. 17, 2014 for Japanese Application No. 20130179563 filed Aug. 30, 2013, 7 pages.
Olympus Medical Systems, "Olympus ScopeGuide Receives FDA Clearance," Press Release dated May 24, 2011, 2 pages.
Partial European Search Report for Application No. EP20120840613, dated Jun. 5, 2015, 5 pages.
PCT/US07/71085 Written Opinion, dated Sep. 17, 2008, 5 pages.
PCT/US09/46446 International Search Report and Written Opinion of the International Searching Authority, dated Dec. 14, 2009, 21 pages.
PCT/US09/46446 Partial International Search Report and Invitation to Pay Additional Fees, dated Sep. 18, 2009, 9 pages.
PCT/US2011/035113 International Search Report and Written Opinion of the International Searching Authority, dated Aug. 4, 2011, 13 pages.
Shang, J. et al., "An Articulated Universal Joint Based Flexible Access Robot for Minimally Invasive Surgery," 2011 IEEE Conference on Robotics and Automation (ICRA), May 9-13, 2011, London, UK, pp. 1147-1152.
Stieber, Michael E. et al., "Vision-Based Sensing and Control for Space Robotics Applications," IEEE Transactions on Instrumentation and Measurement, Aug. 1999, vol. 48, No. 4, pp. 807-812.
Sturges, Robert H. et al., "A Flexible, Tendon-Controlled Device for Endoscopy," The International Journal of Robotics Research, 1993, pp. 121-131, vol. 12—Issue 2, SAGE Publications.
Szewczyk, Jerome et al., "An active tubular polyarticulated microsystem for flexible endoscope," Lecture Notes in Control and Information Sciences, vol. 271, Experimental Robotics VII, 2000, pp. 179-188, Springer-Verlag.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Wang, Yi-Ping et al., "A novel long period fiber grating sensor measuring curvature and determining bend-direction simultaneously," IEEE Sensors Journal, 2005, pp. 839-843, vol. 5—Issue: 5, IEEE.
Webster, Robert J. III et al., "Toward Active Cannulas: Miniature Snake-Like Surgical Robots," 2006, 7 pages.
Wong, Allan C. L. et al., "Multiplexed fibre Fizeau interferometer and fibre Bragg grating sensor system for simultaneous measurement of quasi-static strain and temperature using discrete wavelet transform," Measurement Science and Technology, 2006, pp. 384-392, vol. 17—Issue 2, Institute of Physics Publishing.
Lunwei, Zhang et al., "FBG Sensor Devices for Spatial Shape Detection of Intelligent Colonoscope," IEEE International Conference on Robotics and Automation, Apr. 2004, New Orleans, Louisiana, pp. 835-840.
Al-Ahmad A., et al., "Early Experience with a Computerized Obotically Controlled Catheter System," Journal of Interventional Cardiac Electrophysiology, Apr. 2005, vol. 12(3), pp. 199-202.
Amended Joint Claim Construction Chart, United States District Court for the District of Delaware, Plaintiffs: *Intuitive Surgical, Inc. and Intuitive Surgical Operations, Inc.,* v. Defendant: *Auris Health, Inc,* Case No. 18-1359-MN, Document 123-1, Nov. 13, 2019, 31 pages.
Amended Joint Claim Construction Chart, United States District Court for the District of Delaware, Plaintiffs: *Intuitive Surgical, Inc. and Intuitive Surgical Operations, Inc.,* v. Defendant: *Auris Health, Inc,* Case No. 18-1359-MN, Document 81, Aug. 29, 2019, 29 pages.
Amending Scheduling Order, United States District Court for the District of Delaware, Plaintiffs: *Intuitive Surgical, Inc. and Intuitive Surgical Operations, Inc.,* v. Defendant: *Auris Health, Inc,* Case No. 1:18-cv-01359-MN, Document 62, 2019, 14 pages.
Auris Health, Inc.'s Opposition to Motion for Reargument Regarding Mar. 11, 2019 Scheduling Order, United States District Court for the District of Delaware, Plaintiffs: *Intuitive Surgical, Inc. and Intuitive Surgical Operations, Inc.,* v. Defendant: *Auris Health, Inc,* Jury Trial Demanded, Case No. 18-1359-MN, Document 52, Mar. 29, 2019, 8 pages.
Compendium of Inventor Declarations in Support of Plaintiffs Intutive Surgical, Inc. and Intutive Surgical Operations, Inc.'s Opposition to Defendant Auris Health, Inc.'s Motion to Transfer, United States District Court for the District of Delaware, Plaintiffs: *Intuitive Surgical, Inc. and Intuitive Surgical Operations, Inc.,* v. Defendant: *Auris Health, Inc,* C.A. No. 18-1359-MN, Document 29, Dec. 11, 2018, 2 pages.
Complaint for Patent Infringement, United States District Court for the District of Delaware, Plaintiffs: *Intuitive Surgical, Inc. and Intuitive Surgical Operations, Inc.,* v. Defendant: *Auris Health, Inc,* Demand for Jury Trial, Aug. 31, 2018, 14 pages
Curriculum Vitae of Prof. Ron Alterovitz, Ph.D, Professor, Department of Computer Science, University of North Carolina at Chapel Hill, Jan. 14, 2019, 22 pages.
Declaration of Prof. Ron Alterovitz, United States District Court for the District of Delaware, Plaintiffs: *Intuitive Surgical, Inc. and Intuitive Surgical Operations, Inc.,* v. Defendant: *Auris Health, Inc,* Case No. 1:18-cv-01359-MN, 2019, 25 pages.
Declaration of Professor Mark E. Rentschler, Ph.D, Mar. 2018, 58 pages.
Declaration of David Styka in Support of Defendant Auris Health, Inc.'s Opening Brief in Support of Its Motion to Transfer Venue Pursuant to 28 U.S.C. § 1404(A), United States District Court for the District of Delaware, Plaintiffs: *Intuitive Surgical, Inc. and Intuitive Surgical Operations, Inc.,* v. Defendant: *Auris Health, Inc,* Case No. 1:18-cv-01359-LPS, Jury Trial Demanded, Document 18, 2018, 3 pages.
Declaration of Kelly E. Farnan in Support of Auris Health, Inc.'s Opposition to Motion for Reargument Regarding Mar. 11, 2019 Scheduling Order, United States District Court for the District of Delaware, Plaintiffs: *Intuitive Surgical, Inc. and Intuitive Surgical Operations, Inc.,* v. Defendant: *Auris Health, Inc,* Case No. 18-1359-MN, Document 53, 2019, 3 pages.
Declaration of Laura E. Miller in Support of Plaintiffs' Opposition to Defendant's Motion to Stay, United States District Court for the District of Delaware, Plaintiffs: *Intuitive Surgical, Inc. and Intuitive Surgical Operations, Inc.,* v. Defendant: *Auris Health, Inc,* Case No. 18-1359-MN, Exihibit, Document 122, Nov. 13, 2019, 50 pages.
Declaration of Laura Miller in Support of Plaintiffs' Motion for Reargument Regarding Mar. 11, 2019 Scheduling Order, United States District Court for the District of Delaware, Plaintiffs: *Intuitive Surgical, Inc. and Intuitive Surgical Operations, Inc.,* v. Defendant: *Auris Health, Inc,* Case No. 18-1359-MN, Document 44, 2019, 1 page.
Declaration of Nathan B, Sabri in Support of Defendant Auris Health, Inc.'s Opening Brief in Support of Its Motion to Transfer Venue Pursuant to 28 U.S.C. § 1404(A), United States District Court for the District of Delaware, Plaintiffs: *Intuitive Surgical, Inc. and Intuitive Surgical Operations, Inc.,* v. Defendant: *Auris Health, Inc,* Case No. 1:18-cv-01359-LPS, Jury Trial Demanded, Document 16, 2018, 7 pages.

(56) References Cited

OTHER PUBLICATIONS

Declaration of Shaelyn K. Dawson in Support of Defendant Auris Health, Inc.'s Motion to Stay Case Pending Inter Partes Review, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 119, 2019, 3 pages.

Declaration of Shaelyn K. Dawson in Support of Defendant Auris Health, Inc.'s Reply in Support of Its Motion to Stay Case Pending Inter Partes Review, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-MN, Document 127, 2019, 2 pages.

Declaration of Taylor Patton in Support of Plaintiffs Intuitive Surgical, Inc. and Intuitive Surgical Operations, Inc.'s Opposition to Defendant Auris Health, Inc.'s Motion to Transfer, United States District Court for the District of Delaware, Plaintiffs: *Intuitive Surgical, Inc. and Intuitive Surgical Operations, Inc.*, v. Defendant: *Auris Health, Inc*, Redacted—Public Version, C.A. No. 18-1359-MN, Document 30, Dec. 11 , 2018, 15 pages.

Declaration of Vera Ranieri in Support of Plaintiffs Intuitive Surgical, Inc. and Intuitive Surgical Operations, Inc.'s Opposition to Defendant Auris Health, Inc.'s Motion to Transfer, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-MN, Document 28, Demand for Jury Trial, 2018, 4 pages, Defendant Auris Health, Inc.'s Amended Notice of Deposition of Catherine J. Mohr, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-MN, Demand for Jury Trial, Document 99, Oct. 9, 2019, 2 pages.

Defendant Auris Health, Inc.'s Amended Notice of Deposition of Vincent Duindam, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-MN, Document 100, Demand for Jury Trial, Oct. 9, 2019, 2 pages.

Defendant Auris Health, Inc.'s Answer to Plaintiffs' Complaint for Patent Infringement, United States District Court for the District of Delaware, Plaintiffs: *Intuitive Surgical, Inc. and Intuitive Surgical Operations, Inc.*, v. Defendant: *Auris Health, Inc*, Case No. 18-1359-LPS, Jury Trial Demanded, Document 12, Oct. 25, 2018, 12 pages.

Defendant Auris Health, Inc.'s Notice of 30(B)(6) Deposition of Intuitive Surgical, Inc. and Intuitive Surgical Operations, Inc, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 120, Nov. 12, 2019, 10 pages.

Defendant Auris Health, Inc.'s Notice of Deposition of Catherine J. Mohr, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 94, Oct. 2, 2019, 2 pages.

Defendant Auris Health, Inc.'s Notice of Deposition of Mark E. Rentschler, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Demand for Jury Trial, Document 103, Oct. 15, 2019, 2 pages.

Defendant Auris Health, Inc.'s Notice of Deposition of Tim Soper, United States District Court for the District of Delaware, Plaintiffs: *Intuitive Surgical, Inc. and Intuitive Surgical Operations, Inc.*, v. Defendant: *Auris Health, Inc*, Demand for Jury Trial, Case No. 18/1359-MN, Document 87, Sep. 13, 2019, 2 pages.

Defendant Auris Health, Inc.'s Notice of Deposition of Vincent Duindam, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 93, Oct. 2, 2019, 2 pages.

Defendant Auris Health, Inc.'s Opening Brief in Support of Its Motion to Stay Case Pending Inter Partes Review, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Jury Trial Demanded, Document 118, Oct. 30, 2019, 18 pages.

Defendant Auris Health, Inc.'s Opening Brief in Support of Its Motion to Transfer Venue Pursuant to 28 U.S.C. § 1404(a), United States District Court for the District of Delaware, Plaintiffs: *Intuitive Surgical, Inc. and Intuitive Surgical Operations, Inc.*, v. Defendant: *Auris Health, Inc*, Case No. 18-1359-LPS, Jury Trial Demanded, Document 15, Oct. 29, 2018, 25 pages.

Defendant Auris Health, Inc.'s Preliminary Invalidity Contentions, Demand for Jury Trial, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, 2019, 38 pages.

Defendant Auris Health, Inc.'s Reply Brief in Support of Its Motion to Stay Pending Inter Partes Review, United States District Court for the District of Delaware, Demand for Jury Trial, Plaintiffs: *Intuitive Surgical, Inc. and Intuitive Surgical Operations, Inc.*, v. Defendant: *Auris Health, Inc*, Case No. 18-1359-MN, Document 126, Nov. 15, 2019, 13 pages.

Defendant Auris Health, Inc.'s Reply Brief in Support of Its Motion to Transfer Venue Pursuant to 28 U.s.c. § 1404(a), United States District Court for the District of Delaware, Plaintiffs; *Intuitive Surgical, Inc. and Intuitive Surgical Operations, Inc.*, v. Defendant: *Auris Health, Inc*, C.A. No. 18-1359-MN, Document 31, Nov. 18, 2018, 14 pages.

Defendant Auris Health, Inc.'s Supplemental Corporate Disclosure Statement Per F.r.c.p. 7.1, United States District Court for the District of Delaware, Plaintiffs: *Intuitive Surgical, Inc. and Intuitive Surgical Operations, Inc.*, v. Defendant: *Auris Health, Inc*, Jury Trial Demanded, Case No. 18-1359-MN, Apr. 17, 2019, 2 pages.

Defendant's Corporate Disclosure Statement per F.R.C.P. 7.1(a), United States District Court for the District of Delaware, Plaintiffs: *Intuitive Surgical, Inc. and Intuitive Surgical Operations, Inc.*, v. Defendant: *Auris Health, Inc*, Case No. 18-1359-LPS, Jury Trial Demanded, Document 13, Oct. 25, 2018, 1 page.

Excerpts from Merriam-Webster's Collegiate Dictionary, 2003, 11th Edition, 3 pages.

Excerpts from the deposition of Mark Edwin Rentschler, Ph.D., Oct. 21, 2019, 35 pages.

Exhibit 1, Plaintiffs Intuitive Surgical, Inc. and Intuitive Surgical Operations, Inc.'s Preliminary Election of Asserted Claims, United States District Court for the District of Delaware, Plaintiffs; *Intuitive Surgical, Inc. and Intuitive Surgical Operations, Inc.*, v. Defendant: *Auris Health, Inc*, Case No. 1:18-cv-01359-MN, Demand for Jury Trial, Document 119-1, Aug. 9, 2019, 5 pages.

Exhibit 1, Declaration, Annual Report Pursuant to Section 13 or 15(D) of the Securities Exchange Act of 1934, United States Securities and Exchange Commission, Form 10-K, Case 1:18-cv-01359-MN, Intuitive Surgical, Inc, Document 28-1, 2018, 12 pages.

Exhibit 1, Fox Chase Cancer Center Among First in U.S. to Use Innovative Technology for Lung Cancer Diagnosis, Temple Health, Retrieved from the Internet: (https://vvww.foxchase.org/news/2018-08-15-Monarch-Robotic-Bronchoscopy), Case 1:18-cv-01359-MN, Document 23-3, Aug. 15, 2018, 4 pages.

Exhibit 1, Morrison & Foerster, via Email, *Intuitive Surgical, Inc.* v. *Auris Health, Inc*, Case No. 1:18-cv-01359-MN, Sep. 9, 2019, Document 127-1, 22 pages.

Exhibit 1, [Proposed] Scheduling Order, United States District Court for the District of Delaware, Plaintiffs: *Intuitive Surgical, Inc. and Intuitive Surgical Operations, Inc.*, v. Defendant: *Auris Health, Inc*, Demand for Jury Trial, Case No. 1:18-cv-01359-MN, Document 43-2, 2019, 14 pages.

Exhibit 10, "Auris Health Lands $220M to Expand Sales of Lung Testing Medical Robot, " exome, Frank Vinluan, Case 1:18-cv-01359-MN, Document 28-10, 2018, 4 pages.

Exhibit 10, From: Dawson, Shaelyn K, Subject: *Intuitive* v. *Auris*: Summary of Sep. 26, 2019 meet-and-confer re: Intuitive's deficient production, Case 1:18-cv-01359-MN, Document 119-10, 2019, 4 pages.

(56) References Cited

OTHER PUBLICATIONS

Exhibit 11, "Auris Health Lands $220M to Expand Sales of Lung Testing Medical Robot, " Xcomony, Nov.28, 2018, Auris, Auris Health, Inc , Case 1:18-cv-01359-MN, Document 28-11, 2018, 4 pages.
Exhibit 11, U.S Food and Drug Administration, Case 1:18-cv-01359-MN, Document 119-11, Auris Surgical Robotics, Inc, Mar. 22, 2018, 12 pages.
Exhibit 12, United States Securities and Exchange Commission, Form D, Notice of Exempt Offering of Securities, Case 1:18-cv-01359-MN, Document 28-12, 2018, 7 pages.
Exhibit 13, United States Securities and Exchange Commission, Form D, Notice of Exempt Offering of Securities, Case 1:18-cv-01359-MN, Document 28-13, 2018, 7 pages.
Exhibit 14, "Auris Surgical Robotics Agrees to Acquire Hansen Medical," Market Wired, Source: Hansen Medical, Inc, The Global Leader in Intravascular Robotics, Case 1:18-cv-01359-MN, Document 28-14, Apr. 20, 2016, 2018, 4 pages.
Exhibit 15, Declaration, Delaware, U.S. District Court , Case 1:18-cv-01359-MN, Document 28-15, 2018, 3 pages.
Exhibit 2, Declaration, "Pairing Human Ingenuity with Technology," Intuitive, Case 1:18-cv-01359-MN, Document 28-2, 2018, 13 pages.
Exhibit 2, Petition for Inter Partes Review of U.S. Pat. No. 8,801,601, USPTO, Petitioner: Auris Health, Inc, Patent Owner Intuitive Surgical Operations, Inc, Case 1:18-cv-01359-MN, Document 119-2, Inter Partes Review No. IPR2019-01173, Jun. 12, 2019, 85 Pages.
Exhibit 2, [proposed] Scheduling Order, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-MN, Document 43-3, 2019, 19 pages.
Exhibit 2, UPMC Hamot First in U.S. to Use Innovative Robotic Technology to Detect Lung Cancer Earlier, UPMC Life Changing Medicine, Case No. 1:18-cv-01359-MN, Document 23-4, 2018, 3 pages.
Exhibit 3, Declaration, Contact Intuitive, Office locations and contact Information, Case 1:18-cv-01359-MN, Document 28-3, 2018, 5 pages.
Exhibit 3, Letter, Careers Audacious goals. Audacious challenges, Auris Health Inc, Retrieved from the Internet: (https://www.aurishealth.com/jobs?gh_jid=1256912), 2018, Case 1:18-cv-01359-MN, Document 23-5, 7 pages.
Exhibit 3, Petition for Inter Partes Review of U.S. Pat. No. 6,800,056, USPTO, Petitioner: Auris Health, Inc, Patent Owner Intuitive Surgical Operations, Inc, Case 1:18-cv-01359-MN, Document 119-3, Inter Partes Review No. IPR2019-01189, Jun. 13, 2019, 73 Pages.
Exhibit 4, "da Vinci Robotic Surgery," Christiana Care Health System, Helen F. Graham Cancer Center & Research Institute, Case 1:18-cv-01359-MN, Document 28-4, 2018, 3 pages.
Exhibit 4, Letter, Robotic Bronchoscopy for Peripheral Pulmonary Lesions, ClinicalTrials.gov, Document 23-6, Retrieved from the Internet: (https://clinicaltrials.gov/ct2/show/NCT03727425), Auris Health, Inc, Case 1:18-cv-01359-MN, Document 23-6, ClinicalTrials.gov Identifier: NCT03727425, 2018, 9 pages.
Exhibit 4, Petition for Inter Partes Review of U.S. Pat. No. 6,246,200, USPTO, Before the Patent Trial and Appeal Board, Petitioner: Auris Health, Inc, Patent Owner Intuitive Surgical Operations, Inc, Case 1:18-cv-01359-MN, Inter Partes Review No. IPR2019-01448, Document 119-4, Aug. 5, 2019, 86 pages.
Exhibit 5, "Auris Health, Ethicon's Neuwave Ink Robot-assisted Bronchoscope Ablation Dev Deal," May 16, 2018, by Fink Densford, Retrieved from the Internet: (https://https://www.massdevice.com/auris-health-ethicons-neuwave-ink-robot-assisted-bronchoscope-ablation-dev-deal/), Case 1:18-cv-01359-MN, Document 23-7, 2018, Massdevice Medical Network, 12 pages.
Exhibit 5, Declaration, "Beebe Healthcare Introduces the da Vinci® XI™ Robotic Surgical System," Submitted by Rachel on Jun. 8, 2018, Case 1:18-cv-01359-MN, Document 28-5, 4 Pages
Exhibit 5, Petition for Inter Partes Review of U.S. Pat. No. 9,452,276, USPTO, Before the Patent Trial and Appeal Board, Petitioner: Auris Health, Inc, Patent Owner Intuitive Surgical Operations, Inc, Case 1:18-cv-01359-MN, Inter Partes Review No. IPR2019-01496, Document 119-5, Aug. 15, 2019, 72 pages.
Exhibit 6, Declaration, "Fox Chase Cancer Center Among First in U.S. to Use Innovative Technology for Lung Cancer Diagnosis," Philadelphia International Medicine® News Bureau, Fox Chase Cancer Center Temple Health, for Immediate Release, Case 1:18-cv-01359-MN, Document 28-6, Aug. 23, 2018, 3 pages.
Exhibit 6, Letter, Nathan, Morrison & Foerster LLP, *Intuitive Surgical, Inc. et al* v. *Auris Health, Inc.*, C.A. No. 18-1359-LPS, Document 23-8, 2018, 4 pages.
Exhibit 6, Petition for Inter Partes Review of U.S. Pat. No. 8,142,447, Before the Patent Trial and Appeal Board, Petitioner: Auris Health, Inc, Patent Owner Intuitive Surgical Operations, Inc, Case 1:18-cv-01359-MN, Inter Partes Review No. IPR2019-01533, Document 119-6, Aug. 29, 2019, 84 pages.
Exhibit 7, Petition for Inter Partes Review of U.S. Pat. No. 6,491,701, Before the Patent Trial and Appeal Board, Petitioner: Auris Health, Inc, Patent Owner Intuitive Surgical Operations, Inc, Case 1:18-cv-01359-MN, Inter Partes Review No. IPR2019-01532, Document 119-7, Aug. 29, 2019, 79 Pages.
Exhibit 7, "UPMC Hamot First in U.S. to Use Innovative Robotic Technology to Detect Lung Cancer Earlier," UPMC Life Changing Medicine, Case No. 1:18-cv-01359-MN, Document 28-7, 2018, 3 pages.
Exhibit 8, Careers Audacious goals. Audacious challenges, Auris, Retrieved from the Internet: (URL:http://https://www.aurishealth.com/jobs?gh_jid=1256912), Case 1:18-cv-01359-MN, Document 28-8, 2018, 8 pages.
Exhibit 8, Petition for Inter Partes Review of U.S. Pat. No. 6,522,906, USPTO, Before the Patent Trial and Appeal Board, Petitioner: Auris Health, Inc, Patent Owner Intuitive Surgical Operations, Inc, Case 1:18-cv-01359-MN, IPR2019-01547, Document 119-8, Aug. 30, 2019, 82 pages.
Exhibit 9, "Robotic Bronchoscopy for Peripheral Pulmonary Lesions," ClinicalTrials.gov, U.S National Library of Medicine, ClinicalTrials.gov Identifier: NCT03727425, Auris Health, Inc, Case 1:18-cv-01359-MN, Document 28-9, 2018, 8 pages.
Exhibit 9, Trial Statistics, USPTO, Case 1:18-cv-01359-MN, Document 119-9, 2019, 12 pages.
Exhibit A, Da Vinci by Intuitive, enabling Surgical care to get patients back to what matters, Aug. 29, 2019, Case 1:18-cv-01359-MN, Document 114-1, Retrieved from the internet: URL: [https://www.intuitive.com/en-us/products-and-services/da-vinci], pp. 4 pages.
Exhibit A, Intuitive, Annual Report 2017, Intuitive Surgical, Inc, www.intuitivesurgical.com, Case 1:18-cv-01359-MN, Document 16-1, 2018, 144 pages.
Exhibit A, "Johnson & Johnson Announces Agreement to Acquire Auris Health, Inc," Auris Health's Robotic Platform Expands Johnson & Johnson's Digital Surgery Portfolio, New Brunswick, NJ—Feb. 13, 2019, Case 1:18-cv-01359-MN, Document 36-1, 2019, 4 pages.
Exhibit A, Letter,*Intuitive Surgical, Inc. and Intuitive Surgical Operations, Inc.* v. *Auris Health, Inc.*, Case 1:18-cv-01359-MN, Doc 53-1, 2019, 86 pages.
Exhibit A, Plaintiffs Intuitive Surgical, Inc. and Intuitive Surgical Operations, Inc.'s Notice of Deposition under Fed. R. Civ. P. 30(B)(6) Directed to Defendant Auris Health, Inc.'s Motion to Transfer, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-LPS, Demand for Jury Trial, Document 23-1, Dec. 3, 2018, 7 pages.
Exhibit B, Plaintiffs Intuitive Surgical, Inc. and Intuitive Surgical Operations, Inc.'s First Set of Requests for Production of Documents to Defendant Auris Health, Inc, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-LPS, Document 23-2, Dec. 3, 2018, 9 pages.
Extended European Search Report for Application No. EP19174999.3 dated Nov. 26, 2019, 10 pages.
Extended European Search Report for Application No. 12840613.9 dated Oct. 6, 2015, 9 pages.

(56) References Cited

OTHER PUBLICATIONS

Hagn U., et al., "DLR MiroSurge: A Versatile System for Research in Endoscopic Telesurgery," International Journal of Computer Assisted Radiology and Surgery, 2010, vol. 5 (2), 11 pages.
Hansen Medical, Inc., "Bibliography", Jun. 22, 2005, 1 page, retrieved from the internet [URL: https://web.archive.org/web/20060714042735if_/http://hansenmedical.com/bibliography.aspx].
Hansen Medical, Inc., "Sensei: Discover Your Sixth Sense", Brochure, 2007, 10 pages.
Hansen Medical, Inc., "Sensei-X:Robotic Catheter System", Brochure, 2009, 5 pages.
Hansen Medical, Inc., "System Overview", 2005, 2 pages,retrieved from the Internet [URL: https://web.archive.org/web/20060714043118if_/http://hansenmedical.com/system.aspx].
Hansen Medical, Inc., "Technology Advantages", 2005, 1 page,retrieved from the internet [URL: https://web.archive.org/web/20060713011151if_/http://hansenmedical.com/advantages.aspx].
Ion by Intuitive, A New Robotic Endoluminal Platform for Minimally Invasive Peripheral Lung Biopsy, Aug. 29, 2019, Retrived from the internet: [https://www.intuitive.com/en-us/products-andservices/ion], 5 pages.
Joint Claim Construction Brief, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-MN, Document 113, Oct. 29, 2019, 103 pages.
Joint Claim Construction Chart, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 76, Aug. 2, 2019, 31 pages.
Kenneth Salisbury Jr., "The heart of microsurgery," The American Society of Mechanical Engineers , 1998, 12 pages.
Le Roux, P.D., et al., "Robot-assisted Microsurgery: A Feasibility Study in the Rat," Neurosurgery, Mar. 2001, vol. 48 (3), pp. 584-589.
Letter Response, Kelly E. Farnan, by CM/ECF, Richards Layton & Finger, Case 1:18-cv-01359-MN, Document 24, RLF1 20392700v. 1, Document 24, Dec. 4, 2018, 3 pages.
Letter, Shaw Keller LLP, by CM/ECF & Hand Delivery, Case 1:18-cv-01359-MN, Oct. 29, 2019, Document 112, 1 pages.
Marrouche N.F., et al., "AB32-1: Preliminary Human Experience Using a Novel Robotic Catheter Remote Control", May 6, 2005, 1 page.
Memorandum Opinion, United States District Court for the District of Delaware, Plaintiffs: *Intuitive Surgical, Inc. and Intuitive Surgical Operations, Inc.*, v. Defendant: *Auris Health, Inc*, Case No. 18-1359 (MN), May 31, 2019, 13 pages.
Memorandum Order, United States District Court for the District of Delaware, Plaintiffs: *Intuitive Surgical, Inc. and Intuitive Surgical Operations, Inc.*, v. Defendant: *Auris Health, Inc*, Case No. 18-1359 (MN), 2019, 16 pages.
Minute Entry for proceedings held before Judge Maryellen Noreika, Telephone Conference held on Aug. 21, 2019, 1 page.
Motion to Stay, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 117, Oct. 30, 2019, 2 pages.
Nambi M., et al., "A Compact Telemanipulated Retinal—Surgery System that Uses Commercially Available Instruments with a Quick-Change Adapter," Journal of Medical Robotics Research, 2016, vol. 1 (2), 14 pages.
Oh S., et al., "P5-75: Novel Robotic Catheter Remote Control System: Safety and Accuracy in Delivering RF Lesions in All 4 Cardiac Chambers", 2005, pp. S277-S278.
Olympus , Your Vision, Our Future, "Endoscope Overview 2008," Evis Exera II, HDTV 1080, Case 1:18-cv-01359-MN, Document 114-1, 6 pages.
Oral Order, *Intuitive Surgical, Inc. et al* v. *Auris Health, Inc*, 1-18-cv-01359 (DED), docket entry 25, 2018, 1 Page.
Oral Order, re 37 Proposed Scheduling Order, *Intuitive Surgical, Inc. et al* v. *Auris Health, Inc*, 1-18-cv-01359 (DED), 2019, 1 page.
Order Regarding Access to Source Code, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Mar. 21, 2019, 3 pages.
Order Scheduling Adr Teleconference, United States District Court for the District of Delaware, Plaintiffs: *Intuitive Surgical, Inc and Intuitive Surgical Operations, Inc* v. Defendant: *Auris Health, Inc*, Case No. 18-1359-MN, Document 142, 2019, 4 pages.
Order, United States District Court for the District of Delaware, Plaintiffs: *Intuitive Surgical, Inc. and Intuitive Surgical Operations, Inc.*, v. Defendant: *Auris Health, Inc*, Case No. 18-1359 (MN), Document 70, 2019, 1 pages.
Partial European Search Report for Application No. EP19174999.3 dated Aug. 21, 2019, 11 pages.
Patent Owner's Preliminary Response for U.S. Pat. No. 9,452,276, Review No. IPR2019-01496 dated Nov. 22, 2019, 33 pages.
Petitioner's Updated Exhibit List of U.S. Pat. No. 9,452,276, review No. IPR2019-01496 dated Dec. 9, 2019, pp. 1-4.
Plaintiffs' First Notice of Rule 30(B)(6) Deposition of Defendant Auris Health, Inc, United States District Court for the District of Delaware, Plaintiffs: *Intuitive Surgical, Inc. and Intuitive Surgical Operations, Inc.*, v. Defendant: *Auris Health, Inc*, Document 129, Case No. 18-1359-MN, 2019, 14 Pages.
Plaintiffs Intuitive Surgical, Inc. and Intuitive Surgical Operations, Inc.'s Corporate Disclosure Statement, United States District Court for the District of Delaware, Plaintiffs: *Intuitive Surgical, Inc. and Intuitive Surgical Operations, Inc.*, v. Defendant: *Auris Health, Inc*, Aug. 31, 2018, 1 page.
Plaintiffs Intuitive Surgical, Inc. and Intuitive Surgical Operations, Inc.'s Notice of Subpoenas to Produce Documents, Information, or Objects or to Permit Inspection of Premises in a Civil Action, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 82, 2019, 20 pages.
Plaintiffs Intuitive Surgical, Inc. and Intuitive Surgical Operations, Inc.'s Opposition to Defendant Auris Health, Inc.'s Motion to Transfer, United States District Court for the District of Delaware, Plaintiffs: *Intuitive Surgical, Inc, and Intuitive Surgical Operations, Inc.*, v. Defendant: *Auris Health, Inc*, Case No. 18-1359-MN, Document 26, Dec. 11, 2018, 23 pages.
Plaintiffs' Motion for Reargument Regarding Mar. 11, 2019 Scheduling Order, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 43, Mar. 15, 2019, 8 pages.
Plaintiffs' Opposition to Defendant's Motion to Stay, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 121, Nov. 13, 2019, 21 pages.
[Proposed] Amended Scheduling Order, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-MN, Document 61, 2019, 14 pages.
[Proposed] Order Regarding Access to Source Code, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 46, Mar. 21, 2019, 3 pages.
Proposed Order, United States District Court for the District of Delaware, Plaintiffs: *Intuitive Surgical, Inc. and Intuitive Surgical Operations, Inc.*, v. Defendant: *Auris Health, Inc*, C.A. No. 18-1359-MN, Document 43-1, 2019, 1 page.
Proposed Scheduling Order, United States District Court for the District of Delaware, Plaintiffs: *Intuitive Surgical, Inc. and Intuitive Surgical Operations, Inc.*, v. Defendant: *Auris Health, Inc*, Case 1:18-cv-01359-MN, Document 37, 2019, 17 pages.
Proposed Scheduling Order, United States District Court for the District of Delaware, Plaintiffs: *Intuitive Surgical, Inc. and Intuitive Surgical Operations, Inc.*, v. Defendant: *Auris Health, Inc*, Case 18-1359-MN, Document 41, 2019, 17 pages.

(56) References Cited

OTHER PUBLICATIONS

[Proposed] Stipulated Protective Order, United States District Court for the District of Delaware, Plaintiffs: *Intuitive Surgical, Inc. and Intuitive Surgical Operations, Inc.*, v. Defendant: *Auris Health, Inc*, Case No. 18-1359-MN, Document 45, Mar. 21, 2019, 31 pages.
PTAB Teleconference for review No. IPR2019-01496 dated Dec. 6, 2019, Petitioner Auris Health, Inc, pp. 1-33.
Rassweiler J., et al., "The Role of Imaging and Navigation for Natural Orifice Translumenal Endoscopic Surgery," Journal of Endourology, May 2009, vol. 23 (5), pp. 793-802.
Reddy V.Y., et al., "P1-53: Porcine Pulmonary Vein Ablation Using a Novel Robotic Catheter Control System and Real-time Integration of CT Imaging with Electroanatomical Mapping", 2005, p. S121.
Report on the Filing or Determination of an Action Regarding a Patent or Trademark, To: Mail Stop 8, Director of USPTO, Alexandria, VA, Case 1:18-cv-01359-MN, Document 3, 2018, 2 pages.
Rosenberg J.M., Artificial Intelligence & Robotics, 1986, 3 pages.
Rule 7.1.1 Certificate, United States District Court for the District of Delaware, Plaintiffs: *Intuitive Surgical, Inc. and Intuitive Surgical Operations, Inc.*, v. Defendant: *Auris Health, Inc*, Case No. 18-01359-MN, Document 117-2, Oct. 30, 2019, 2 pages.
Scheduling Order, United States District Court for the District of Delaware, Plaintiffs: *Intuitive Surgical, Inc. and Intuitive Surgical Operations, Inc.*, v. Defendant: *Auris Health, Inc*, C.A. No. 18-1359-MN, Document 42, 2019, 17 pages.
Shaw Keller LLP, Letter, Karen E. Keller, Case 1:18-cv-01359-MN, *Intuitive Surgical, Inc., et al.* v. *Auris Health, Inc.*, Document 23, by CM/ECF & Hand Delivery, Dec. 3, 2018, 4 pages.
Shaw Keller LLP, Letter Proposed Scheduling Order, by CM/ECF & Hand Delivery, Case 1:18-cv-01359-MN, Document 39, Feb. 28, 2019, 1 page.
Shaw Keller LLP, Letter to Request Scheduling of a Discovery Teleconference, By CM/ECF & Hand Delivery, Case 1:18-cv-01359-MN, Document 20, Nov. 8, 2018, 1 page.
Shaw Keller LLP, Letter, Written to Advise the Court that Auris has "Entered into a Definitive Agreement", By CM/ECF & Hand Delivery, Case 1:18-cv-01359-MN, Document 36, Feb. 20, 2019, 1 page.
Sheila Weller, He Helped Pioneer Robotic Surgery. Now He Wants to Reinvent Lung Cancer Care, JNJ.com, Apr. 2019, Case 1:18-cv-01359-MN, Document 114-2, Retrived from the internet : [https://www.jnj.com/personal-stories/why-robotic-surgery-pioneer-frederic-moll-is-now-tackling-lung-cancer-care], 6 pages.
Slepian M.J., "Robotic Catheter Intervention: The Hansen Medical Sensei™ Robotic Catheter System," 2010, 28 pages.
Sturges R.H. Jr., et al., "A Voice-Actuated, Tendon-Controlled Device for Endoscopy", 1996, pp. 603-617.
Super Dimension, "How it Works", 2005, 2 pages, retrieved from the Internet [URL: https://web.archive.org/web/20070510094239/http://www.superdimension.com/new_resources.html].
Super Dimension, "Overview", 2005, 2 pages, retrieved from the internet [URL: https://web.archive.org/web/20070510094239/http://www.superdimension.com/new_resources.html].
Super Dimension, "System Elements", 2005, 2 pages, retrieved from the internet [URL: https://web.archive.org/web/20070510094239/http://www.superdimension.com/new_resources.html].
Supplemental Briefing Regarding Claim Construction Arguments and Rulings in Parallel District Court Action of U.S. Pat. No. 9,452,276, Review No. IPR2019-01496 dated Dec. 13, 2019, 5 pages.
Tab 1, "Declaration of Stephen J, Blumenkranz in Support of Plaintiffs Intuitive Surgical, Inc. and Intuitive Surgical Operations, Inc.'s Opposition to Defendant Auris Health, Inc.'s Motion to Transfer," United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-MN, Demand for Jury Trial, Case 1:18-cv-01359-MN, Document 29-1, 2018, 3 pages.
Tab 2, "Declaration of Thomas G. Cooper in Support of Plaintiffs Intuitive Surgical, Inc. and Intuitive Surgical Operations, Inc.'s Opposition to Defendant Auris Health, Inc.'s Motion to Transfer," United States District Court for the District of Delaware, Plaintiffs: *Intuitive Surgical, Inc. and Intuitive Surgical Operations, Inc.*, v. Defendant: *Auris Health, Inc*, Demand for Jury Trial, Case No. 1:18-cv-01359-MN, Document 29-2, 2018, 3 pages.
Tab 3, "Declaration of Nicola Diolaiti in Support of Plaintiffs Intuitive Surgical, Inc, and Intuitive Surgical Operations, Inc.'s Opposition to Defendant Auris Health, Inc.'s Motion to Transfer," United States District Court for the District of Delaware, Plaintiffs: *Intuitive Surgical, Inc. and Intuitive Surgical Operations, Inc.*, v. Defendant: *Auris Health, Inc*, Demand for Jury Trial, Case No. 1:18-cv-01359-MN, Document 29-3, 2018, 3 pages.
Tab 4, "Declaration of Vincent Duindam in Support of Plaintiffs Intuitive Surgical, Inc. and Intuitive Surgical Operations, Inc.'s Opposition to Defendant Auris Health, Inc.'s Motion to Transfer," Demand for Jury Trial, United States District Court for the District of Delaware, Plaintiffs: *Intuitive Surgical, Inc. and Intuitive Surgical Operations, Inc.*, v. Defendant: *Auris Health, Inc*, Case No. 1:18-cv-01359-MN, Document 29-4, Demand for Jury Trial, 2018, 3 pages.
Tab 5, "Declaration of Carolyn M. Fenech in Support of Plaintiffs Intuitive Surgical, Inc. and Intuitive Surgical Operations, Inc.'s Opposition to Defendant Auris Health, Inc.'s Motion to Transfer," United States District Court for the District of Delaware, Plaintiffs: *Intuitive Surgical, Inc. and Intuitive Surgical Operations, Inc.*, v. Defendant: *Auris Health, Inc*, Demand for Jury Trial, Case No. 1:18-cv-01359-MN, Document 29-5, 2018, 3 pages.
Tab 6, "Declaration of Gary S. Guthart in Support of Plaintiffs Intuitive Surgical, Inc. and Intuitive Surgical Operations, Inc.'s Opposition to Defendant Auris Health, Inc.'s Motion to Transfer," United States District Court for the District of Delaware, Plaintiffs: *Intuitive Surgical, Inc. and Intuitive Surgical Operations, Inc.*, v. Defendant: *Auris Health, Inc*, Demand for Jury Trial, Case No. 1:18-cv-01359-MN, Document 29-6, 2018, 3 pages.
Tab 7, "Declaration of Catherine J. Mohr in Support of Plaintiffs Intuitive Surgical, Inc. and Intuitive Surgical Operations, Inc.'s Opposition to Defendant Auris Health, Inc.'s Motion to Transfer," Demand for Jury Trial, Case 1:18-cv-01359-MN, Document 29-7, 2018, 3 pages.
Tab 8, "Declaration of Robert Matthew Ohline in Support of Plaintiffs Intuitive Surgical, Inc. and Intuitive Surgical Operations, Inc.'s Opposition to Defendant Auris Health, Inc.'s Motion to Transfer," United States District Court for the District of Delaware, Plaintiffs: *Intuitive Surgical, Inc. and Intuitive Surgical Operations, Inc.*, v. Defendant: *Auris Health, Inc*, Demand for Jury Trial, Case No. 1:18-cv-01359-MN, Document 29-8, 2018, 3 pages.
Tab 9, "Declaration of David J. Rosa in Support of Plaintiffs Intuitive Surgical, Inc. and Intuitive Surgical Operations, Inc.'s Opposition to Defendant Auris Health, Inc.'s Motion to Transfer," United States District Court for the District of Delaware, Plaintiffs: *Intuitive Surgical, Inc. and Intuitive Surgical Operations, Inc.*, v. Defendant: *Auris Health, Inc*, Demand for Jury Trial, Case No. 1:18-cv-01359-MN, Document 29-9, 2018, 3 pages.
The Da Vinci Surgical system, Retrieved from the Internet: [http://web.archive.org/web/20080724022504/http:/www.intuitivesurgical.com/products/davinci_surgicalsystem/], 2 pages.
Transcript Teleconference, United States District Court for the District of Delaware, Plaintiffs: *Intuitive Surgical, Inc. and Intuitive Surgical Operations, Inc.*, v. Defendant: *Auris Health, Inc*, Case No. 18-1359(MN), Document 58, 2019, 11 pages.
Transcript, United States District Court for the District of Delaware, Plaintiffs: *Intuitive Surgical, Inc. and Intuitive Surgical Operations, Inc.*, v. Defendant: *Auris Health, Inc*, Case No. 18-1359-(MN), Document 83, 9 pages.
Waldman H., Dictionary of Robotics, 1985, 4 pages.
Markman Hearing, Before: The Honorable Maryellen Noreika, Case No. 18/1359(MN), Plaintiffs; Intuitive Surgical, Inc., Defendant: Auris Health, Inc., held on Nov. 20, 2019, pp. 1-162.
Order Conduct of the Proceeding, Before the Patent Trial and Appeal Board,Case IPR2019-01173, Case IPR2019-01189, Case IPR2019-01496, Case IPR2019-01547, Dated Dec. 9, 2019, 4 pages.

(56) References Cited

OTHER PUBLICATIONS

Patent Owner's Mandatory Notices of U.S. Pat. No. 9,452,276, Before the Patent Trial and Appeal Board, Petitioner: Auris Health, Inc, Patent Owner: Intuitive Surgical Operations, Inc, IPR2019-01496, Sep. 3, 2019, 6 pages.

Patent Owner's Response to Supplemental Paper Regarding Claim Construction Arguments and Rulings in a Related District Court Action of U.S. Pat. No. 9,452,276, Review No. IPR2019-01496 dated Dec. 20, 2019, 4 pages.

Petitioner's Updated Exhibit List of U.S. Pat. No. 9,452,276, review No. IPR2019-01496 dated Oct. 15, 2019, 4 pages.

Petitioner's Updated Exhibit List of U.S. Pat. No. 9,452,276, review No. IPR2019-01496 dated Dec. 5, 2019, pp. 1-4.

* cited by examiner

ELECTROMAGNETIC SENSOR WITH PROBE AND GUIDE SENSING ELEMENTS

CROSS-REFERENCE TO RELATED APPLICATIONS

This patent document is a divisional of U.S. patent application Ser. No. 13/889,984, filed May 8, 2013, which claims the priority of U.S. provisional Pat. App. No. 61/646,619, filed May 14, 2012, and is a continuation-in-part and claims benefit of the earlier filing date of U.S. patent application Ser. No. 13/274,237, filed Oct. 14, 2011, all of which are hereby incorporated by reference in their entirety.

BACKGROUND

Minimally invasive medical devices that navigate natural body lumens need to be small enough to fit within the lumens. Lung catheters, for example, which may be used to perform minimally invasive lung biopsies or other medical procedures, may need to follow airways that decrease in size as the catheter navigates branching passages. To reach a target location in a lung, a catheter may follow passages having diameters as small as 3 mm or less. Manufacturing a catheter that is sufficiently small and includes the mechanical structures and sensors for remote or robotic operation can be challenging.

Electromagnetic sensors (EM) sensors can measure the position and orientation of a portion of a medical instrument. EM sensors are particularly suitable for minimally invasive medical instruments because EM sensors can combine high global accuracy with a small diameter package size. During EM sensor operation, a generator external to a patient can produce a well-controlled, time-varying magnetic field, and in response, one or more coils of an EM sensor in or on a portion of the medical instrument produce induced electrical signals. In particular, time variations in the magnetic field induce currents in the coils of the EM sensor, and the pose of each coil can be partially determined from knowledge of the generated magnetic field and the geometry of the coil. A single coil can be used, for example, to measure a position and a pointing direction, e.g., pitch and yaw angles, but a cylindrically symmetrical coil is unable to distinguish roll angles about the symmetry axis of the coil. Accordingly, EM sensors employing a single cylindrical coil have been used as 5-Degree-of-Freedom (5-DoF) sensors. To additionally measure the roll angle, a 6-DoF EM sensor generally requires two coils having symmetry axes that are not parallel, e.g., perpendicular symmetry axes.

The long, thin shape typical of 5-DoF EM sensors fits well with minimally invasive medical instruments or tools, which often have long and thin extensions. However, with the central axis of a single coil sensor aligned with the roll axis of an instrument, such 5-DoF EM sensors cannot measure the roll angle of the instrument. While some symmetric instruments such as needles may not require roll angle measurements, many instruments require knowledge of the roll angle of the instrument, particularly for robotic control. Measurement of the roll angle may require a 6-DoF sensor that includes two coils. For example, to create a 6-DoF EM sensor, two 5-DoF EM sensors may need to be placed perpendicular or at a non-zero angle to each other, which creates a much larger sensor package. If each 5-DoF sensor has a cylindrical shape about 1 mm in diameter and about 10 mm long, the 6-DoF sensor containing two 5-DoF sensors may be up to 10×10×1 mm. While the 1 mm diameter of a 5-DoF EM sensor may fit within a small, e.g., 3 mm diameter, instrument, a 10-mm wide 6-DoF EM sensor may not fit in a small instrument.

SUMMARY

In accordance with an aspect of the invention, a small diameter EM sensor can include a coil with windings that define areas with a normal direction at a significant angle to the symmetry or long axis of the coil. As a result, the magnetic axis of an EM sensor that extends along a length of an instrument may be at an angle to the roll axis of the instrument to enable the sensor to measure a roll angle of the instrument, while still providing a narrow diameter package.

In one specific embodiment, a sensing system uses a coil including wire that is wound in loops around an axis, and each of the loops defines an area that has a normal direction at a non-zero, angle relative to the axis of the coil.

In another embodiment, a sensing system includes a coil and sensor logic. The coil includes wire that is wound in loops about an axis, and the loops define respective areas that have a normal direction at a non-zero angle relative to the axis of the coil. The sensor logic is coupled to the coil and configured to use an electrical signal induced in the coil in determining a measurement of a roll angle about the axis of the coil.

In yet another embodiment, a medical system includes a probe and optionally a guide instrument (e.g., catheter, bronchoscope, or endoscope) with a lumen sized for guiding the probe. A probe coil is in the probe and includes wire that is wound in loops collectively defining a first core that extends in a lengthwise direction of the probe. However, each of the loops in the probe coil defines an area that has a normal direction at a non-zero angle relative to the length of the probe. A secondary sensor (e.g., an electromagnetic sensor, shape sensor, gravity sensor, visualization sensor, and/or angular sensor(s), among others) included in the medical system can provide supplemental orientation information to be used with the probe coil signals to determine a roll angle of the probe. For example, a secondary sensor such as a coil could be positioned in a wall of a guide instrument for the probe, such that each of the loops of the guide instrument coil defines an area that has a second normal direction. Sensor logic that is coupled to receive induced signals from the probe coil and the guide instrument coil can then determine a roll angle of the probe from the induced signals.

BRIEF DESCRIPTION OF THE DRAWINGS

Use of the same reference symbols in different figures indicates similar or identical items.

DETAILED DESCRIPTION

An EM sensor can employ an off-axis coil, which is a coil wound so that areas respectively defined by individual loops have a normal direction that is off-axis from the length of the coil. As a result, an effective area for magnetic flux in the off-axis coil has a normal direction that is also off-axis from the length of the coil. A magnetic field applied to an off-axis coil can be varied to induce an electrical signal that depends on the normal direction instead of about the long axis of the coil. Such a coil can thus be used in a small-diameter medical instrument to measure a roll angle about the long axis of the coil.

Figure 1:
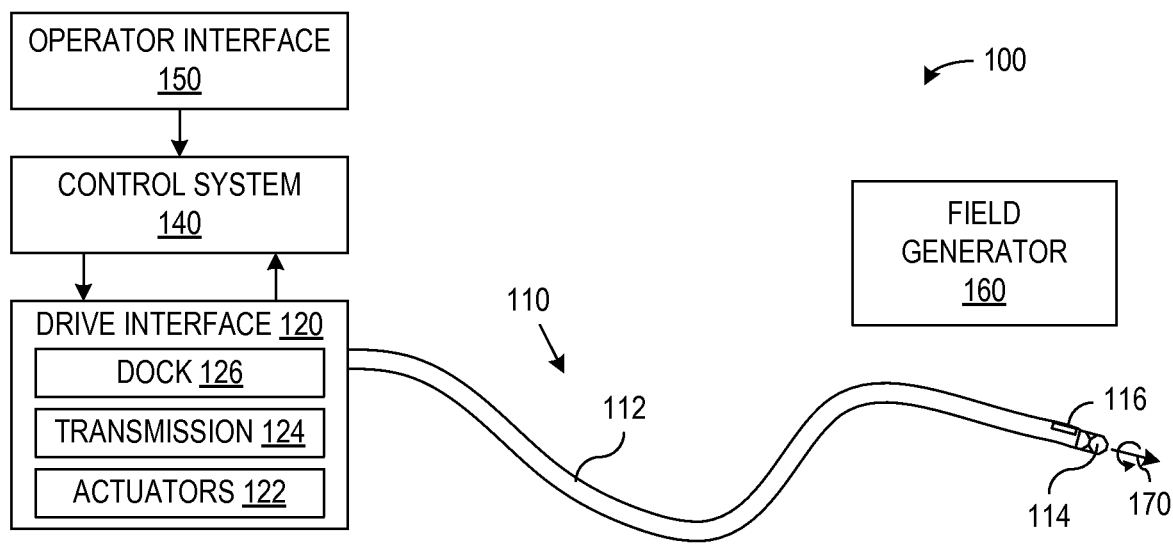
FIG. 1 shows a minimally invasive medical instrument that uses an electromagnetic sensor that includes an off-axis coil.

FIG. 1 schematically illustrates a medical system 100 in accordance with one embodiment of the invention. In the illustrated embodiment, medical system 100 includes a medical device 110, a drive interface 120, a control system 140, an operator interface 150, and a field generator 160 for a sensing system.

Medical device 110, in the illustrated embodiment, may be a flexible device such as a catheter, bronchoscope, endoscope, or cannula that includes a main shaft 112 with one or more lumens. For example, main shaft 112 may include a main lumen sized to accommodate interchangeable probes. Such probes can include a variety of a camera or vision systems, biopsy tools, cutting tools, clamping tools, sealing tools, suturing tools, stapling tools, cautery tools, therapeutic or diagnostic material delivery tools, or any other surgical instruments. The probes used in device 110 may be robotically operated, for example, using actuating tendons (not shown) that run the length of the probe. Additionally, main shaft 112 may incorporate one or more steerable sections 114 that are similarly operable using actuating tendons that attach to steerable section 114 and run from steerable section at the distal end of main shaft 112, through main shaft 112, to the proximal end of main shaft 112.

An exemplary embodiment of device 110 may be a lung catheter, bronchoscope or endoscope, where device 110 would typically be about 60 to 80 cm or longer. During a medical procedure, at least a portion of main shaft 112 and all of steerable section 114 may be inserted along a natural lumen such as an airway of a patient, and drive interface 120 may operate steerable section 114 by pulling on actuating tendons, e.g., to steer device 110 during insertion or to position steerable section 114 for a procedure.

Figure 2:
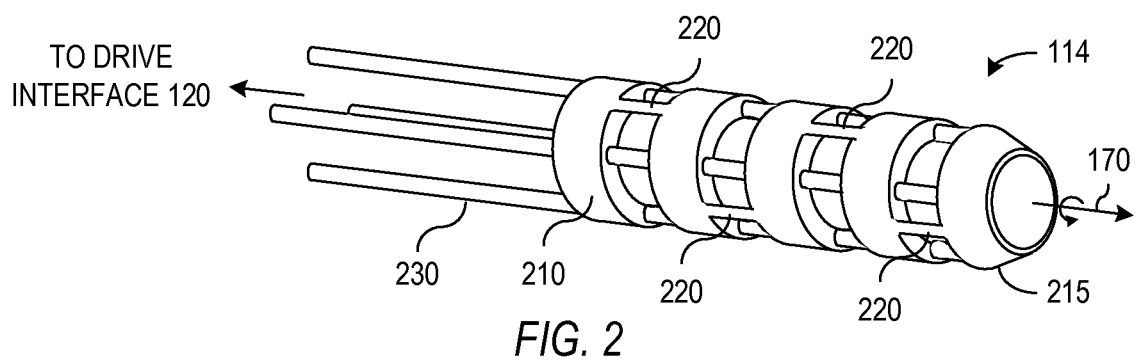
FIG. 2 shows an embodiment of a steerable segment that can be employed in the system of FIG. 1.

Steerable section 114 is remotely controllable and particularly has a pitch and a yaw that can be controlled using actuating tendons, e.g., pull wires or cables, and may be implemented as a multi-lumen tube of flexible material such as Pebax. In general, steerable section 114 may be more flexible than the remainder of main tube 112, which assists in isolating actuation or bending to steerable section 114 when drive interface 120 pulls on the actuating tendons. Device 110 can also employ additional features or structures such as use of Bowden cables for actuating tendons to prevent actuation from bending the more proximal portion of main tube 112. In general, the actuating tendons are located at different angles about a roll axis 170 of steerable section 114. For example, FIG. 2 shows one specific embodiment in which steerable section 114 is made from a tube 210 that may be cut to create flexures 220. Tube 210 in the illustrated embodiment defines a main lumen for a probe system and smaller lumens for actuating tendons 230. In the illustrated embodiment, four actuating tendons 230 attach to a distal tip 215 of steerable section 114 at locations that are 90° apart around a roll axis 170 of steerable section 114. In operation, pulling harder on any one of tendons 230 tends to cause steerable section 114 to bend in the direction of that tendon 230. To accommodate repeated bending, tube 210 may be made of a material such as Nitinol, which is a metal alloy that can be repeatedly bent with little or no damage.

Actuating tendons 230 extend back through main tube 112 to drive interface 120 and may be coated or uncoated, single filament or multi strand wires, cables, Bowden cables, hypotubes, or any other structures that are able to transfer force from drive interface 120 to distal tip 215. (Push rods could conceivably be used in device 110 instead of tendons 230 but may not provide a desirable level of flexibility needed in some medical instruments.) Tendons 230 can be made of any material of sufficient strength including but not limited to a metal such as steel or a polymer such as Kevlar.

Drive interface 120 of FIG. 1, which pulls on actuating tendons 230 to operate steerable section 114, includes a mechanical system or transmission 124 that converts the movement of actuators 122, e.g., electric motors, into movements of (or tensions in) actuating tendons 230. The movement and pose of steerable section 114 can thus be controlled through selection of drive signals for actuators 122 in drive interface 120. In addition to manipulating the actuating tendons, drive interface 120 may also be able to control other movement of device 110 such as a range of motion in an insertion direction and rotation or roll of the proximal end of device 110, which may also be powered through actuators 122 and transmission 124. Backend mechanisms or transmissions that are known for flexible-shaft instruments could in general be used or modified for drive interface 120.

A dock 126 in drive interface 120 of FIG. 1 can provide a mechanical coupling between drive interface 120 and device 110 and link the actuating tendons 230 to transmission 124. Dock 126 may additionally contain an electronic or optical system for receiving, converting, and/or relaying sensor signals from one or more EM sensors 116 and contain an electronic or mechanical system for identifying the specific probe or the type of probe deployed in device 110.

Control system 140 controls actuators 122 in drive interface 120 to selectively pull on the actuating tendons as needed to actuate or steer steerable section 114. In general, control system 140 operates in response to commands from a user, e.g., a surgeon or other medical personnel using operator interface 150, and in response to measurement signals such as from EM sensors 116. Control system 140 may in particular include or execute sensor logic that analyzes signals (or digitized versions signals) from EM sensors 116 to determine measurement of the position and orientation of the distal end of device 110. Control system 140 may be implemented using a general purpose computer with suitable software, firmware, and/or interface hardware to interpret signals from operator interface 150 and EM sensors 116 and to generate control signals for drive interface 120.

Operator interface 150 may include standard input/output hardware such as a display, a keyboard, a mouse, a joystick, or other pointing device or similar I/O hardware that may be customized or optimized for a surgical environment. In general, operator interface 150 provides information to the user and receives instructions from the user. For example, operator interface 150 may indicate the status of system 100 and provide the user with data including images and measurements made by system 100. One type of instruction that the user may provide through operator interface 150, e.g., using a joystick or similar controller, indicates the desired movement or position of steerable section 114, and using such input, control system 140 can generate control signals for actuators in drive interface 120.

Field generator 160 and one or more EM sensors 116 can be used to measure a pose of a distal portion of main tube 112 or of steerable section 114. EM sensors 116 may particularly include an off-axis coil that field generator 160 may subject to a magnetic field that varies over space or time. The magnetic field produces magnetic flux through EM sensors 116, and variation in time of that magnetic flux induces a voltage or electric current in EM sensors 116.

The induced signals can be used to measure the pose of EM sensor 116. For example, U.S. Pat. No. 7,197,354, entitled "System for Determining the Position and Orientation of a Catheter"; U.S. Pat. No. 6,833,814, entitled "Intrabody Navigation System for Medical Applications"; and U.S. Pat. No. 6,188,355, entitled "Wireless Six-Degree-of-Freedom Locator" describe the operation of some EM sensor systems and are hereby incorporated by reference in their entirety. U.S. Pat. No. 7,398,116, entitled "Methods, Apparatuses, and Systems useful in Conducting Image Guided Interventions," U.S. Pat. No. 7,920,909, entitled "Apparatus and Method for Automatic Image Guided Accuracy Verification," U.S. Pat. No. 7,853,307, entitled "Methods, Apparatuses, and Systems Useful in Conducting Image Guided Interventions," and U.S. Pat. No. 7,962,193, entitled "Apparatus and Method for Image Guided Accuracy Verification" further describe systems and methods that can use electromagnetic sensing coils in guiding medical procedures and are also incorporated by reference in their entirety.

Figure 3:
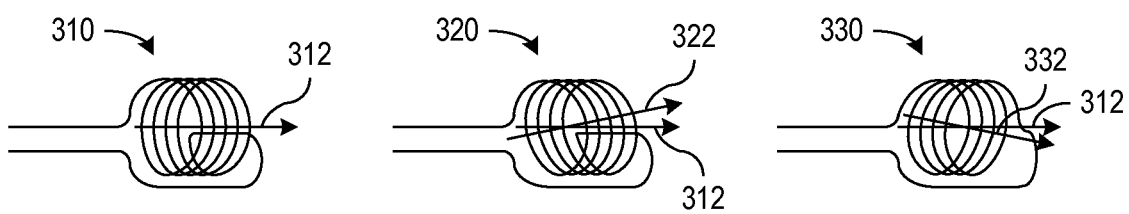
FIG. 3 shows sensing coils that can be employed in electromagnetic sensors in medical systems in some embodiments of the invention.

FIG. 3 illustrates three different types of sensing coils 310, 320, and 330 that could be used in an EM sensor. Coil 310 is a helical coil containing individual loops defining areas that are substantially perpendicular to a lengthwise axis 312 of coil 310. A field generator can vary the direction and magnitude of the magnetic field in a systematic manner that enables at least partial determination of the pose of coil 310 from the induced electric signal. In particular, up to five degrees of freedom can be measured using sensing coil 310. However, sensing coil 310 is cylindrically symmetric, so that a roll angle, i.e., an angle indicating orientation about axis 312 of coil 310, cannot be determined from an electric signal induced in coil 310. However, the position and the pointing direction of coil 310 can be determined from the induced electrical signal and knowledge of the generated magnetic field. Accordingly, coil 310 can be used for a 5-DoF sensor that measures position X, Y, and Z and pointing angles θ and φ, but a 5-DoF sensor using coil 310 alone cannot measure a roll angle ψ.

Coils 320 and 330 of FIG. 3 are off-axis coils. In particular, coil 320 (or 330) includes wire loops with a normal direction 322 (or 332) that is at a non-zero angle to lengthwise axis 312 passing through the loops of coil 320 (or 330). As a result, even when the lengths of coils 310, 320, and 330 are parallel or aligned, coils 320 and 330 are capable of measuring five degrees of freedom that differ from the five degrees of freedom that coil 310 can measure. EM sensor 116 of system 100 can include one or more off-axis coils such as coil 320 or 330 oriented along the length of device 110 to enable measurement of a roll angle of the distal tip of device 110.

Figure 4:
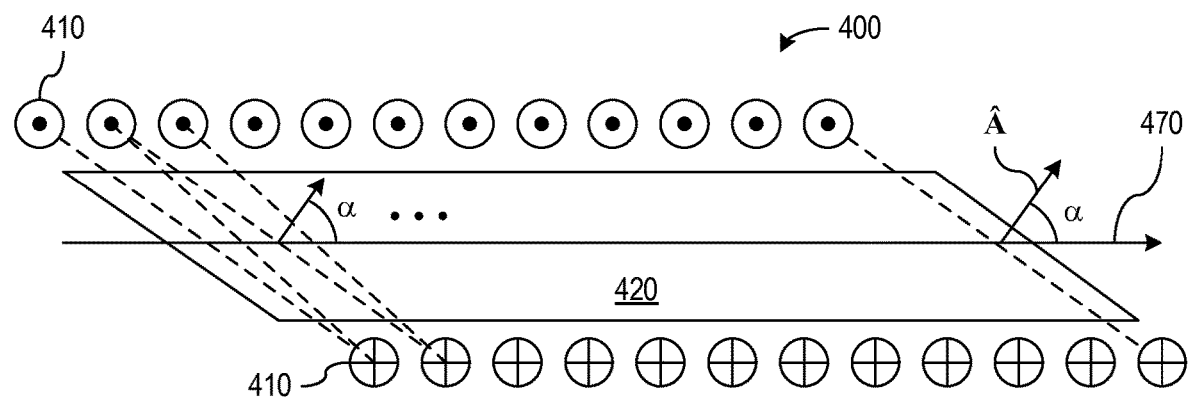
FIG. 4 shows a cross-section of an off-axis coil that can be used in an electromagnetic sensor.

FIG. 4 shows a cross-sectional view of an off-axis coil 400 that may be used in measuring a roll angle. Coil 400 is a winding of wire 410 that may be considered to form multiple loops that define respective areas with a normal direction A. Coil 400 is wound so that normal direction Â is off-axis by an angle α from the length (i.e., from an axis 470) of coil 400. Coil 400 may be formed, for example, by wrapping insulated conductive wire around a core 420 at an angle (90°-α) to axis 470 of core 420 and coil 400 for about one half of each loop and at an angle -(90°-α) for the other half of each loop. As a result, an effective area |A| for magnetic flux in off-axis coil 400 has normal direction Â that is at angle α relative to lengthwise axis 470 of coil 400 and has a magnitude |A| that is equal to the product of the area of a single loop and the number of loops in coil 400. In general, each loop may define an area having any desired shape and may have a shape that depends on angle α and the shape of core 420. For example, each loop area can be elliptical when core 420 is circular cylindrical and angle α is non-zero. For an EM sensor in a medical device, coil 400 may have a diameter of about 1 mm and a length of about 10 mm. The off-axis angle α can be any angle greater than zero and less than 180°, but for roll angle measurement as described further below, angle α may be between about 5° and about 175°. A range for angle α between about 45° to 70° or 110° to 135° for an EM sensor could provide accurate data and avoid difficulties in wrapping a coil when angle α is near 90°.

EM sensors coils such as coil 310 may employ helical coils that are wound so that the normal to the magnetic flux areas are along the lengthwise axis of the coil. In particular, such coils may be helically wound with a constant, slight angle, i.e., the helix angle. For example, the sine of a wrap angle for coil 310 may be about equal to the ratio of the wire thickness to the diameter of coil 310. However, the effects of the wire being at the helix angle around a full loop cancel, and the normal for each loop of coil 310 is along the lengthwise axis. In contrast, the magnitude of the wrap angle (90°-α) in coil 410 can be much greater than the ratio of the diameter of wire 410. Further, for coil 410, the sign of the wrap angle reverses at some point in each loop. As a result, each loop of coil 410 has a part in which the wire angles down core 420 and a part in which the wire angles up core 420.

Figure 5:
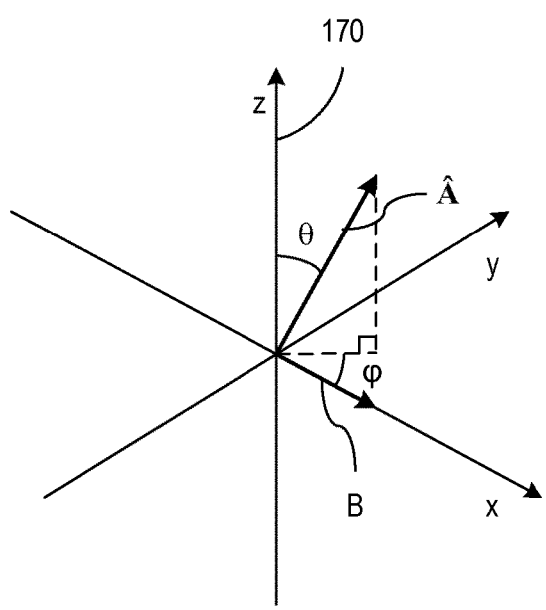
FIG. 5 illustrates the geometry of one embodiment of an electromagnetic sensing system that uses an off-axis coil in a magnetic field for measurements of five degrees of freedom.

A magnetic field B applied to off-axis coil 400 can be varied to induce an electrical signal that depends on the normal direction Â to the areas of the loops forming coil 400. In particular, according to Faradays law, an induced voltage in coil 400 is proportional to the time derivative of the dot product of magnetic field B and an effective area vector |A|Â. FIG. 5 shows one specific geometry for magnetic field B and effective normal vector Â. In FIG. 5, magnetic field B is along the x axis of a Cartesian coordinate system that may be defined relative to a field generator that generates magnetic field B. With this configuration, if only the magnitude |B| of magnetic field B varies with time, the induced signal in coil 400 will have a voltage V given by Equation 1, wherein C is a constant that depends on the magnetic permeability inside coil 400. Since the induced voltage V for coil 400 depends on the direction Â, i.e., angles θ and φ, the direction Â can be determined or measured, by varying the magnitude and direction of magnetic field B and analyzing the change in the induced voltage V. For example, Cartesian coordinates $B_x$, $B_y$, and $B_z$ of the magnetic field B applied to coil 400 can be varied with different frequencies, and the different frequency components of the resulting induced voltage in coil 400 can be analyzed to determine measurements of up to five degrees of freedom of coil 400, including direction angles θ and φ.

(Determining a roll angle ψ may further require knowledge the direction of a roll axis, which may, for example, be measured using a second coil.)

$$V = C|A|\frac{d|B|}{dt}\sin(\theta)\cos(\varphi) \qquad \text{Equation 1}$$

Figure 6A:
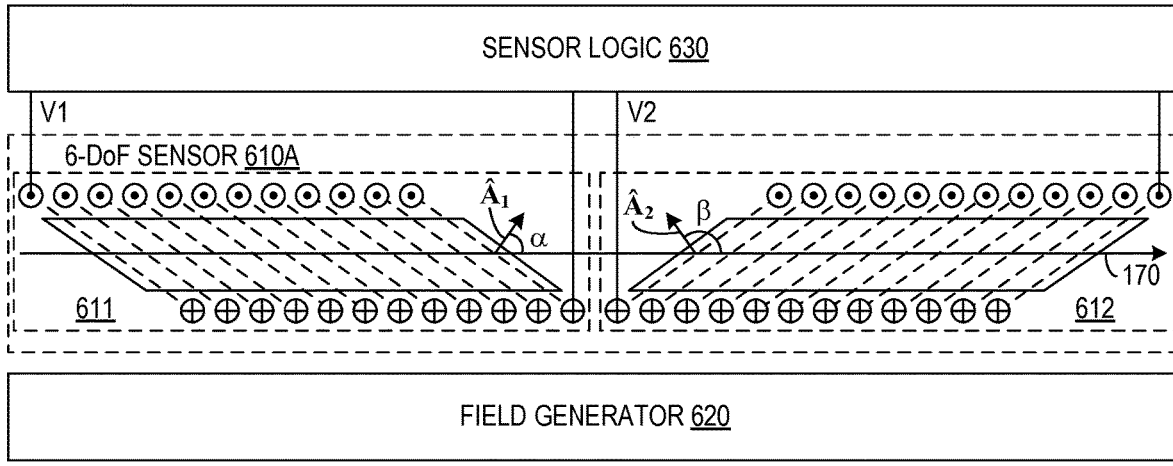
FIGS. 6A and 6B show alternative configurations of electromagnetic sensor systems using at least one off-axis coil for measurement of six degrees of freedom.

Off-axis coils can be employed in small diameter 6-DoF sensors that are well adapted for use in minimally invasive medical instruments, e.g., as EM sensor 116 of FIG. 1. FIG. 6A, for example, shows a sensing system 600A employing coils 611 and 612 having lengths aligned along the same axis 170. Each coil 611 and 612 may have a diameter of about 1 mm or less, so that 6-DoF sensor 610A may similarly have a diameter of about 1 mm or less. One or both of coils 611 and 612 can be an off-axis coil such as coil 410, which is described above with reference to FIG. 4. For coil 611, a normal direction $\hat{A}_1$ of the effective area for magnetic flux is at an angle α to axis 170. For coil 612, a normal direction $\hat{A}_2$ of the effective area for magnetic flux is at an angle β to axis 170. At least one of coils 611 and 612 are off-axis coils, i.e., α≠0 or β≠0, which enables measurement of a roll angle about axis 170.

EM sensing using a single coil can generally only measure a set of five degrees of freedom because a single-coil EM sensor cannot distinguish rotations about the normal direction associated with the effective area of its coil. Two coils 611 and 612 with different normal directions $\hat{A}_1$ and $\hat{A}_2$ are used in sensor system 600A, so that each of coils 611 and 612 measures a different set of five degrees of freedom. In particular, a field generator 620 can produce a variable magnetic field that passes through coils 611 and 612. Coils 611 and 612 then produce respective induced voltages V1 and V2, and sensor logic 630 can process signal V1 to determine measurements of one set of five degrees of freedom and process signal V2 to determine measurements of a different set of five degrees of freedom. Sensor logic 630, which may include software for analyzing digitized versions of signals V1 and V2, can account for the difference in position of coils 611 and 612 and generate measurements of six degrees of freedom, e.g., position coordinates X, Y, and Z and pitch, yaw, and roll angles.

Coils 611 and 612 in the specific configuration illustrated in FIG. 6A are identical off-axis coils, but are oriented so coil 612 is rotated by 180°, e.g., about a yaw axis of sensor 610A, relative to coil 611. As a result, angle β of a normal direction $\hat{A}_2$ to axis 170 is the supplement to angle α, i.e., β=180°-α. Sensing system 600A may be able to achieve highest accuracy measurements if normal directions $\hat{A}_1$ and $\hat{A}_2$ are perpendicular to each other, and in one particular configuration of sensor 610A, angle α is 45° to make normal directions $\hat{A}_1$ and $\hat{A}_2$ perpendicular. If coils 611 and 612 are not identical, a wide range of combinations of angles α and β are possible that make normal directions $\hat{A}_1$ and $\hat{A}_2$ perpendicular, e.g., configurations where |β-α|=90°.

Figure 6B:
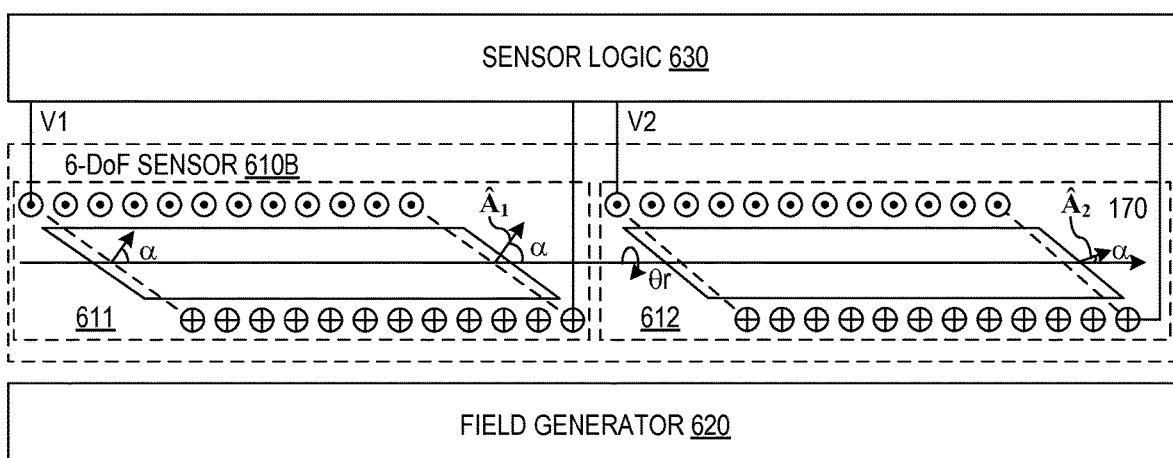

FIG. 6B shows another sensing system 600B using a 6-DoF sensor 610B containing two identical off-axis coils 611 and 612. Coils 611 and 612 in FIG. 6B have respective normal directions $\hat{A}_1$ and $\hat{A}_2$, both of which are at angle α with roll axis 170. However, coil 612 is rotated by an angle θr about roll axis 170 relative to coil 611. In this configuration, normal directions $\hat{A}_1$ and $\hat{A}_2$ are at an angle to each other that depends on angles α and θr. If angle α is greater than or equal to 45°, at least one value for angle θr exists that will make normal directions $\hat{A}_1$ and $\hat{A}_2$ perpendicular. For example, in one configuration, angle α is 45°, angle θr is 180°, and normal directions $\hat{A}_1$ and $\hat{A}_2$ are perpendicular.

Figure 7:
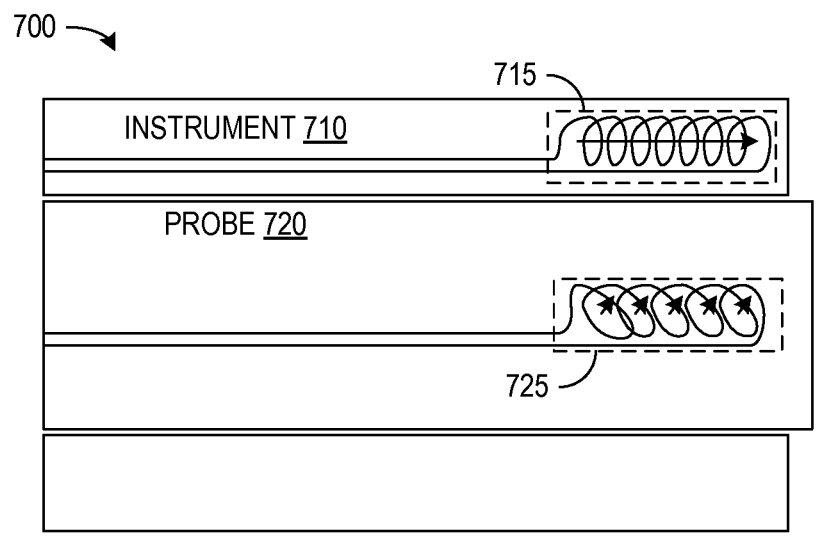
FIG. 7 shows a medical system capable of using a coil in a probe and a secondary sensor to measure six degrees of freedom including a roll angle of the probe.

FIG. 7 shows a medical system 700 capable of measuring six degrees of freedom using a sensing element 715 in an instrument 710 and a coil 725 in a probe 720 that fits within instrument 710. Instrument 710 may be or may include a catheter, a cannula, bronchoscope, endoscope, cannula, or similar instrument through which a probe-like object with unknown roll angle may fit. Sensing element 715 is a device suitable for measurement of at least a pointing direction of the distal tip of instrument 710. As described above, a conventional helical coil can be used to measure five degrees of freedom including a pointing direction of a distal tip of system 700 when such a coil is oriented along a lengthwise axis of system 700, and sensing element 715 could be a coil. Alternatively, sensing element 715 could be another type of sensing device such as a shape sensor, a gravity sensor, a joint angle sensor (for jointed rigid-link instruments), or a vision-based sensor. Note that although described as a system including both a guide instrument 710 and a corresponding probe 720 for exemplary purposes, in various other embodiments, both sensing element 715 and coil 725 can be incorporated into a single instrument.

Coil 725 is an off-axis coil, which can measure five degrees of freedom and when combined with a measurement of a pointing direction of the roll axis can be used to determine a roll angle as described above. Accordingly, the combination of sensing element 715 in instrument 710 and off-axis coil 725 in probe 720 can provide a 6-DoF measurement of probe 720 including measurement of a roll angle of probe 720. An advantage of system 700 is that the use of a single sensing element 715 in instrument 710 may provide additional space in instrument 710 and probe 720 for other structures, which is particularly important for small diameter devices such as lung catheters. Additionally, in system 700, coil 725, which is in probe 720, may be closer to the center of the distal tip than is sensing element 715, which is in the wall of instrument 710. As a result, the roll axis of coil 725 may closely correspond to the roll axis of system 700 and probe 720. Sensing element 715 in instrument 710 may as indicated above be a conventional helical coil so that a measurement of the direction of the area normal of sensing element 715 indicates the direction of the roll axis, and a measurement of the area normal direction of coil 725 can then give the roll angle of probe 720. Alternatively, sensing element 715 could be an off-axis coil, and if the normal direction of the areas defined by the loops in sensing element 715 differs from the normal direction of the areas defined by the loops in coil 725.

System 700 may be used by inserting probe 720 through instrument 710 until the distal ends of instrument 710 and probe 720 are aligned. Probe 720 may, for example, be a camera or vision system that is inserted in instrument 710 for navigation of natural lumens such as lung airways. Instrument 710 with the vision probe may then be steered to a worksite where measurements determined using sensing element 715 and coil 725 are used when orienting the distal tip of instrument 700 for a medical function such as biopsying tissue. The vision probe can then be removed and a probe such as a biopsy needle may be inserted in instrument 710 in place of the vision probe. The biopsy probe may similarly contain a coil or EM sensor, but the EM sensor used then may or may not need to be an off-axis coil or a coil intended for use with sensing element 715. For example, a biopsy needle may be inserted past the distal tip of instrument 710, and the position of the tip of the biopsy needle may be important to measure while the roll angle of a symmetric needle does not need to be measured.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A medical system comprising:
   a probe comprising a terminal distal end;
   a first coil in the probe;
   a guide instrument comprising a terminal distal end and defining a lumen sized to guide the probe, wherein the probe is configured to be inserted through the lumen to reach a worksite, and wherein at the worksite, the terminal distal end of the probe is configured to reach at least the terminal distal end of the guide instrument;
   a sensor embedded in a wall of the guide instrument; and
   processing hardware configured to receive a first induced signal from the first coil and to receive from the sensor an indication of a pointing direction of the guide instrument, the processing hardware being configured to use both the first induced signal from the first coil and the indication of the pointing direction from the sensor to determine a roll angle of the probe.

2. The system of claim 1, wherein the probe comprises one of a surgical tool, a camera, or a vision system.

3. The system of claim 1, wherein the guide instrument comprises one of a catheter, an endoscope, a bronchoscope, or a cannula.

4. The system of claim 3, wherein the probe comprises one of a surgical tool, a camera, or a vision system.

5. The system of claim 1, wherein:
   the sensor comprises a second coil in the guide instrument; and
   the processing hardware is configured to receive a second induced signal from the second coil and employ the second induced signal as the indication of the pointing direction.

6. The system of claim 5, further comprising a field generator configured to generate a varying magnetic field that induces the first induced signal in the first coil and induces the second induced signal in the second coil.

7. The system of claim 5, wherein the second coil is a helical coil.

8. The system of claim 1, wherein the first coil comprises wire that is wound in a plurality of loops collectively defining a first core extending along a lengthwise direction of the probe, wherein each of the loops defines a first normal direction that is at a non-zero angle relative to the lengthwise direction.

9. The system of claim 1, wherein the processing hardware is configured to use the first induced signal and the indication of the pointing direction from the sensor to determine six degrees of freedom of the probe.

10. The system of claim 1, wherein the first coil is the only coil in the probe.

11. The system of claim 1, wherein the processing hardware is configured to receive the first induced signal and the indication of the pointing direction when the probe is at the worksite.

12. The system of claim 11, wherein after the processing hardware receives the first induced signal and the indication of the pointing direction, the probe is configured to be removed from the lumen of the guide instrument.

13. The system of claim 1, wherein the guide instrument further comprises:
    a proximal section;
    a steerable distal section; and
    a plurality of actuation cables extending from the proximal section into the steerable distal section,
    wherein each actuation cable of the plurality of actuation cables is configured to actuate the steerable distal section.

14. The system of claim 13, further comprising an actuator, wherein each actuation cable of the plurality of actuation cables is coupled to the actuator, and wherein the actuator is configured to actuate the steerable distal section of the guide instrument by actuating each actuation cable of the plurality of actuation cables.

15. The system of claim 1, wherein:
    the sensor comprises a shape sensor; and
    the processing hardware is configured to receive a second signal from the shape sensor and employ the second signal as the indication of the pointing direction.

16. The system of claim 1, wherein a roll axis of the probe extends in a direction normal to the sensor in the guide instrument.

17. The system of claim 1, further comprising a surgical tool sized to extend within the lumen of the guide instrument, wherein a terminal distal end of the surgical tool is configured to reach at least the terminal distal end of the guide instrument.

18. The system of claim 17, wherein the surgical tool includes a biopsy needle.

19. The system of claim 17, wherein the surgical tool includes a second coil, and wherein the processing hardware is configured to receive a second induced signal from the second coil and to use both the second induced signal from the second coil and the indication of the pointing direction from the sensor to determine a roll angle of the surgical tool.

20. The system of claim 19, wherein the surgical tool includes an asymmetric biopsy needle, and wherein the processing hardware is configured to determine the roll angle of the surgical tool when the surgical tool extends past the terminal distal end of the guide instrument.

* * * * *